(12) United States Patent
Müller et al.

(10) Patent No.: US 8,409,840 B2
(45) Date of Patent: Apr. 2, 2013

(54) RECOMBINANT PREPARATION OF SELECTED BROMELAIN FRACTIONS

(75) Inventors: Rolf Müller, Blieskastel (DE); Nora Luniak, Saarbrücken (DE); Klaus Eschmann, Kleinblittersdorf (DE)

(73) Assignee: Ursapharm Arzneimittel GmbH, Saarbruecken (DE)

( * ) Notice: Subject to any disclaimer, the term of this patent is extended or adjusted under 35 U.S.C. 154(b) by 219 days.

(21) Appl. No.: 12/678,280

(22) PCT Filed: Aug. 8, 2008

(86) PCT No.: PCT/EP2008/006564
§ 371 (c)(1),
(2), (4) Date: Jul. 6, 2010

(87) PCT Pub. No.: WO2009/033536
PCT Pub. Date: Mar. 19, 2009

(65) Prior Publication Data
US 2010/0272659 A1  Oct. 28, 2010

(30) Foreign Application Priority Data
Sep. 14, 2007 (EP) .................... 07018125

(51) Int. Cl.
*C12N 9/50* (2006.01)
*A61K 38/48* (2006.01)
*C12N 1/19* (2006.01)

(52) U.S. Cl. .......... 435/212; 435/69.1; 435/254.11; 435/254.23; 424/94.65; 514/5.5; 514/846

(58) Field of Classification Search .................. None
See application file for complete search history.

(56) References Cited

U.S. PATENT DOCUMENTS

| 3,658,651 A | 4/1972 | Golding |
| 4,286,064 A | 8/1981 | Galbraith |
| 2002/0188107 A1 | 12/2002 | Mynott et al. |
| 2005/0142633 A1* | 6/2005 | Glaser et al. ............. 435/68.1 |
| 2011/0252501 A1* | 10/2011 | Abad et al. .............. 800/275 |

FOREIGN PATENT DOCUMENTS

| CN | 1186118 | 7/1998 |
| WO | WO 00/03729 A | 1/2000 |
| WO | WO 00/14253 A | 3/2000 |
| WO | WO 2005/096804 A | 10/2005 |

OTHER PUBLICATIONS

Altschul, S.F. et al., "Basic local alignment search tool," Journal of Molecular Biology, 1990, vol. 215, pp. 403-410.
Altschul, S.F. et al., "Gapped BLAST and PSI-BLAST: a new generation of protein database search programs," Nucleic Acids Research, 1997, vol. 25, No. 17, pp. 3389-3402.

(Continued)

*Primary Examiner* — Manjunath Rao
*Assistant Examiner* — William W Moore
(74) *Attorney, Agent, or Firm* — Knobbe Martens Olson & Bear LLP

(57) ABSTRACT

The present invention pertains in general to Bromelain and particularly to the different active compounds contained in this complex mixture of proteins. The present invention provides recombinant expressed cysteine proteases, which are found in Bromelain. It has been found that the method for expression of the recombinant proteins is superior to the purification from Bromelain itself.

9 Claims, 9 Drawing Sheets

Figure 3:
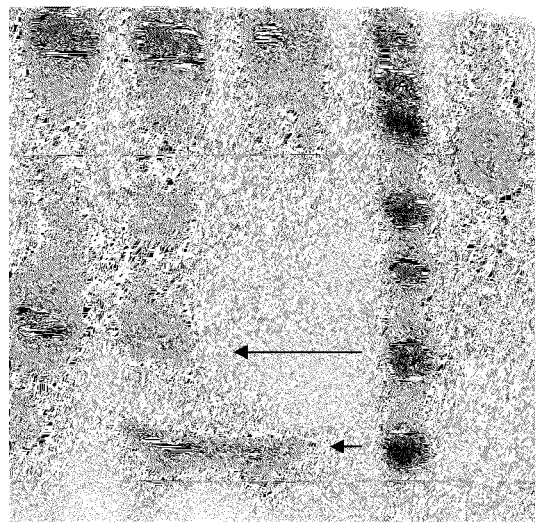

```
                                        351                   384
         Proprotease   (O. sativum)    (301) CGIAQMASYPV------------------
      Procathepsin L  (H. sapiens)     (301) CGIASAASYPTV-----------------
             Propapain (C. papaya)     (330) CGLYTSSFYPVKN----------------
      Procathepsin L  (M. musculus)    (322) CGLATAASYPVVN----------------
                  AN1  (A. comosus)    (322) CGIAMDPLYPTLQSGPSVEVI--------
                  STB4 (A. comosus)    (323) CGIAIDPLYPTLESGANVEAIKMVSESRSSV
                  STB3 (A. comosus)    (323) CGIAIDSLYPTLESRANVEAIKMVSESRSSV
        Fruit bromelain (A. comosus)   (324) CGIAMDPLYPTLQSGANVAVIKMVSKT----
                   FB1 (A. comosus)    (322) CGIAMAPLFPTLQSGANAEVIKMVSET----
        Cysteine protease (V. mungo)   (331) CGIAMMASYPIKNSSDNPTGSLSSPKDEL--
```

OTHER PUBLICATIONS

Brien, S., Bromelain as a treatment of osteoarthritis: a review of clinical studies, Evidence-Based Complementary and Alternative Medicine, 2004, vol. 1(3), pp. 251-257.
Brömme, D. et al., "Production and activation of recombinant papain-like cysteine proteases," Methods, 2004, vol. 32, pp. 199-206.
Carter, Carol et al., Mutagenesis and kinetic studies of a plant cysteine proteinase with an unusual arrangement of acidic amino acids in and around the active site, Biochemistry, Sep. 12, 2000, vol. 39, Issue 36, pp. 11005-11013.
Cregg, J.M. et al., Recent advances in the expression of foreign genes in Pichia pastoris, Biotechnology (N.Y.), 1993, vol. 11, pp. 905-910.
Cregg, J.M. et al., Recombinant protein expression in pichia pastoris, Molecular Biotechnology, Sep. 2000, vol. 16, Issue 1, pp. 23-52, Totowa, NJ, US.
Database EMBL [Online], "Ananas comosus mRNA for ananain precursor, complete cds," XP002472345, retrieved from EBI accession No. EMBL:ACAJ2477, database accession No. AJ002477, Nov. 14, 1997.
Database UniProt [Online], "FBSB precursor," XP002472346, retrieved from EBI accession No. UNIPROT:O23799, database accession No. O23799, Jan. 1, 1998.
Database UniProt [Online], "Fruit bromelain precursor (EC 3.4.22.33) (Allergen Ana c 2)," XP002472347, retrieved from EBI accession No. UNIPROT:O23791, database accession No. O23791, Jan. 1, 1998.
Gupta, Pawan et al., Bioaffinity based oriented immobilization of stem bromelain, Biotechnology Letters, Jun. 8, 2006, vol. 28, Issue 12, pp. 917-922.
International Search Report dated Nov. 4, 2008 for PCT/EP2008/006564.
Luniak, N., Heterologe Expression von Proteinen aus Ananas comosus zur Aufklärung der pharmakologischen Wirkmechanismen von Bromelain, Universität des Saarlandes, Oct. 30, 2007, Saarbrücken, Germany.
Maurer, H.R., Bromelain: biochemistry, pharmacology and medical use, CMLS Cellular and Molecular Life Sciences, Aug. 2001, vol. 58, Issue 9, pp. 1234-1245, Heidelberg, Germany.
Modern Nutrition in Health and Disease, 8th Edition, Lea & Febiger, 1994, vol. 1, pp. 30-32.
Mynott T. et al., "Bromelain, from pineapple stems, proteolytically blocks activation of extracellular regulated Kinase-2 in T cells," The Journal of Immunology, 1999, vol. 163, Issue 5, pp. 2568-2575.
Orsini, R.A., "Bromelain," Plastic and Reconstructive Surgery, Dec. 2006, vol. 118(7), pp. 1640-1644.
Sellers, P., "Pattern recognition in genetic sequences by mismatch density," Bulletin of Mathematical Biology, 1984, vol. 46, No. 4, pp. 501-514.
Shimomura, O. et al., "Extraction, purification and properties of aequorin, a bioluminescent protein from the luminous hydromedusan, aequorea," J. Cell. Comp. Physiol., 1962, vol. 59, pp. 223-239.
Shimomura, O. et al., "The discovery of aequorin and green fluorescent protein," Journal of Microscopy, Jan. 2005, vol. 217, pp. 3-15.
Smith et al., "Identification of common molecular subsequences,", Journal of Molecular Biology, 1981, vol. 147, pp. 195-197.
Thompson et al., Clustal W: improving the sensitivity of progressive multiple sequence alignment through sequence weighting, position-specific gap penalties and weight matrix choice, Nucleic Acids Research, 1994, vol. 22, pp. 4673-4680.
Written Opinion dated Nov. 4, 2008 for PCT/EP2008/006564.
Borgheresi, Rosa A.M.B. et al., Expression and processing of recombinant sarafotoxins precursor in pichia pastoris, Toxicon, Aug. 2001, vol. 39, Issue 8, pp. 1211-1218.
Bretthauer R.K. et al., Glycosylation of pichia pastoris-derived proteins, Biotechnology and Applied Biochemistry, Academic Press, Jan. 1, 1999, vol. 30, pp. 193-200.
Bretthauer R.K., Genetic engineering of pichia pastoris to humanize N-glycosylation of proteins, Trends in Biotechnology, Elsevier Publications, Nov. 1, 2003, vol. 21, Issue 11, pp. 459-462.
Daly R. et al., Expression of heterologous proteins in pichia pastoris: A useful experimental tool in protein engineering and production, Journal of Molecular Recognition, Heyden & Son Ltd., Mar. 1, 2005, vol. 18, Issue 2, pp. 119-138.
Database UniProt [Online], RecName: Full=Bromelain inhibitor; Short=BI; Short=Bromein; Contains: RecName: Full=Bromelain inhibitor 1 chain B; Short=BI-I B; AltName: Full=Bromelain inhibitor VII light chain, XP002524246 retrieved from EBI accession No. UNIPROT:P01068, Database accession No. P01068.
Hatano, Ken-Ichi et al., Structure-function relationship of bromelain isoinhibitors from pineapple stem, Biological Chemistry, Walter de Gruyter GmbH & Co., Jul. 1, 2002, vol. 383, Issue 7-8, pp. 1151-1156.
Martinez-Ruiz A. et al., Secretion of recombinant pro- and mature fungal alpha-sarcin ribotoxin by the methylotrophic yeastPichia pastoris: The Lys-Arg motif is required for maturation, Protein Expression and Purification, Academic Press, Apr. 1, 1998, vol. 12, Issue 3, pp. 315-322.
Qi, Rui-Feng et al., Structural features and molecular evolution of Bowman-Birk protease inhibitors and their potential application, Acta Biochimica et Biophysica Sinica, May 2005, vol. 37, Issue 5, pp. 283-292.
Sawano, Yoriko et al., Characterization of genomic sequence coding for bromelain inhibitors in pineapple and expression of its recombinant isoform, The Journal of Biological Chemistry, Aug. 2, 2002, vol. 277, Issue 31, pp. 28222-28227.
Sawano, Yoriko et al., Susceptibility of the interchain peptide of a bromelain inhibitor precursor to the target proteases bromelain, chymotrypsin, and trypsin, Biological Chemistry, Walter de Gruyter GmbH & Co., May 1, 2005, vol. 386, Issue 5, pp. 491-498.

* cited by examiner

Fig. 1

|  |  |  | 305 | 147 | 170 | 193 | 199 |
|---|---|---|---|---|---|---|---|
| stem. Brom. | STB2 | (An8CAA08860) | YWIVK | NQNPCGACWAFAAIATVESIYKIK | | GGWEFR | AFEFIISNK |
| | STB3 | (BAA22544) | YWIVK | NQNPCGACWAFAAIATVESIYKIK | | GGWEFR | AFEFIISNK |
| | STB4 | | YWIVK | NQNPCGACWAFAAIATVESIYKIK | | GGWEFR | AFEFIISNK |
| | STB1 | (S03964) | -IIYP | NQNPCGACWAFAAIATVESIYKIK | | GGWEFR | AFEFIISNK |
| Ananain | AN1 | (CAA05487) | FWIVR | NQCRCGSCWAFASIATVESIYKIK | | GGWINK | AYSFIISNK |
| | An11CAA08861 | | FWIVR | NHIPCGSCWAFAAIATVESIYKIK | | GGWVNK | AYDFIISNK |
| fruit Brom. | BAA21848 | | YWIVK | DQNPCGSCWAFSAIATVEGIYKIV | | GGFVDN | AYDFIISNN |
| | BAA21929 | | YWIVK | DQNPCGSCWAFSAIATVEGIYKIV | | GGFVDN | AYDFIISNN |
| | BAA22543 | | YWIVK | DQNPCGSCWAFSAIATVEGIYKIV | | GGFVDN | AYDFIISNN |
| | BAA22545 | | YWIVK | DQNPCGSCWAFSAIATVEGIYKIV | | GGFVDN | AYDFIISNN |
| | BAA22546 | | YWIVK | NQNPCGSCWAFAAIATVEGIYKIK | | GGWVNK | AYDFIISNN |
| | BAA21849 | | YWIVR | NQNPCGSCWSFAAIATVEGIYKIK | | GGWVNK | AYDFIISNN |
| | FB1 | | YWIVR | NQNPCGSCWSFAAIATVEGIYKIK | | GGWVNK | AYDFIISNN |

Fig. 2

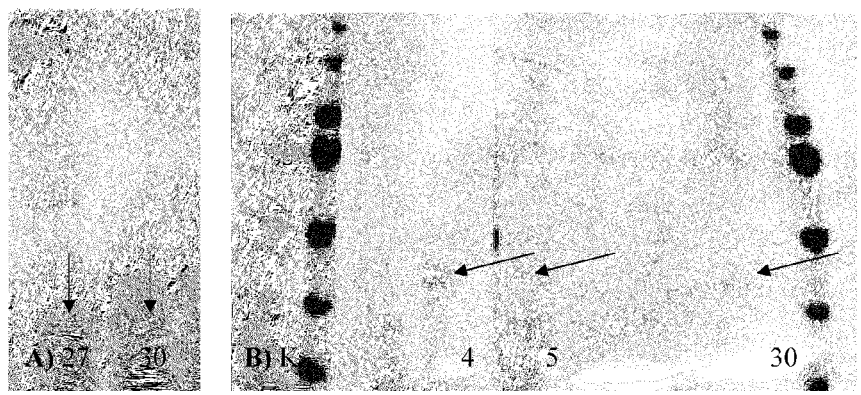

MAWKVQLVFLFLFLCVMWASPSAASADEPSDPMMKRFEEWMVEYGRVYKDNDEK
MRRFQIFKNNVNHIETFNSRNKNSYTLGINQFTDMTNNEFVAQYTGGISRPLNIEREP
VVSFDDVDISAVPQSIDWRDYGAVTSVKNQNPCGACWAFAAIATVESIYKIKKGILE
PLSEQQVLDCAKGYGCKGGWEFRAFEFIISNKGVASAAIYPYKAAKGTCKTNGVPN
SAYITGYARVPRNNESSMMYAVSKQPITVAVDANANFQYYKSGVFNGPCGTSLNHA
VTAIGYGQDSNGKKYWIVKNSWGARWGEAGYIRMARDVSSSSGICGIAIDPLYPTLE
SGANVEAIKMVSESRSSVCGR

Fig. 5b

MAWKVQVVFLFLFLCVMWASPSAASADEPSDPMMKRFEEWMVEYGRVYKDNDE
KMRRFQIFKNNVNHIETFNSRNENSYTLGINQFTDMTNNEFIAQYTGGISRPLNIEREP
VVSFDDVDISAVPQSIDWRDYGAVTSVKNQNPCGACWAFAAIATVESIYKIKKGILE
PLSEQQVLDCAKGYGCKGGWEFRAFEFIISNKGVASGAIYPYKAAKGTCKTNGVPN
SAYITGYARVPRNNESSMMYAVSKQPITVAVDANANFQYYKSGVFNGPCGTSLNHA
VTAIGYGQDSNGKKYWIVKNSWGARWGEAGYIRMARDVSSSSGICGIAIDSLYPTLE
SRANVEAIKMVSESRSSVCGRVD

Fig. 5c

MTSKVQLVFLFLFLCVMWASPSAASCDEPSDPMMKQFEEWMAEYGRVYKDNDEK
MLRFQIFKNNVNHIETFNNRNGNSYTLGINQFTDMTNNEFVAQYTGLSLPLNIKREP
VVSFDDVDISSVPQSIDWRDSGAVTSVKNQGRCGSCWAFASIATVESIYKIKRGNLV
SLSEQQVLDCAVSYGCKGGWINKAYSFIISNKGVASAAIYPYKAAKGTCKTNGVPNS
AYITRYTYVQRNNERNMMYAVSNQPIAAALDASGNFQHYKRGVFTGPCGTRLNHA
IVIIGYGQDSSGKKFWIVRNSWGAGWGEGGYIRLARDVSSSFGLCGIAMDPLYPTLQ
SGPSVEVI

Fig. 5d

MASKVQLVFLFLFLCAMWASPSAASRDEPNDPMMKRFEEWMAEYGRVYKDDDEK
MRRFQIFKNNVKHIETFNSRNENSYTLGINQFTDMTKSEFVAQYTGVSLPLNIEREPV
VSFDDVNISAVPQSIDWRDYGAVNEVKNQNPCGSCWSFAAIATVEGIYKIKTGYLVS
LSEQEVLDCAVSYGCKGGWVNKAYDFIISNNGVTTEENYPYLAYQGTCNANSFPNS
AYITGYSYVRRNDERSMMYAVSNQPIAALIDASENFQYYNGGVFSGPCGTSLNHAIT
IIGYGQDSSGTKYWIVRNSWGSSWGEGGYVRMARGVSSSSGVCGIAMAPLFPTLQS
GANAEVIKMVSETSGRSY

Fig. 6

Fig. 6a atggcttggaaagttcaactcgtgtttcttttcttgtttctctgtgtgatgtgggcttcgccatcggcagcttctgctgacgaacccagtgatc ccatgatgaagcggtttgaagaatggatggtggagtacggccgagtttacaaggacaacgatgagaagatgcgccggtttcagatatt caagaacaacgtgaaccatatcgaaaccttaacagtcgcaataaaaattcgtacactctcggcatcaatcagtttaccgatatgacaaa taacgaatttgttgctcaatatactggtggtatatctcgcccactaaatatcgagagagagccagtggtgtcgtttgatgacgtagacatct ccgcggtgcctcaaagtattgattggagagactacggtgccgtaacaagtgtcaagaaccaaaaccctgtggtgcttgctgggcatt cgctgcaattgcgacggtagaatcaatctacaagatcaaaaaagggatcttagaacctttatcggagcagcaagttctcgattgtgctaa aggctacgggtgcaaaggcggctgggagttcagggccttcgaatttatcatatctaacaagggcgtggcatcggcagctatctaccct tacaaagcagccaaaggcacctgcaagaccaatggcgtgcccaattcagcttatattactggttatgcacgtgtgccgaggaacaacg aaagcagcatgatgtacgctgtgtcgaaacaaccaataactgttgctgtcgatgccaatgcaaactttcaatattacaagagcggtgtgtt taacgggaccttgtggaactagtctcaatcacgctgtcaccgctataggttacgggcaggatagcaackgawaaaaatattggatagt aaagaactcatggggtgccagatggggtgaggccggatacatccgtatggcaagagatgtgtcatcgtcatctggaatatgtggaatc gccattgatcctctctatcccactctagaatcaggggccaatgtcgaagccattaaaatggtttctgaaagtcgaagctcagtggcggcc gcgtaa

Fig. 6b atggcttggaaagttcaagtcgtgtttcttttcttgtttctctgtgtgatgtgggcttcgccatcggcagcttctgctgacgaacccagtgatc ccatgatgaagcggtttgaagaatggatggtggagtacggccgagtttacaaggacaacgatgagaagatgcgccggtttcagatatt

Fig. 6b (cont.)

caagaacaacgtgaaccatatcgaaacttttaacagtcgcaacgaaaattcgtacactctcggcatcaatcagtttaccgatatgacaaa
taacgaatttattgctcaatatactggtggtatatctcgcccactaaatatcgagagagagccagtggtgtcgtttgatgacgtagacatct
ccgcggtgcctcaaagtattgattggagagactacggtgccgtaacaagtgtcaagaaccaaaaccoctgtggtgcttgctgggcatt
cgctgcaattgcgacggtagaatcaatctacaagatcaaaaaagggatcttagaacctttatcggagcagcaagttctcgattgtgctaa
aggctacgggtgcaaaggcggctgggagttcagggccttcgaattcatcatatctaacaagggcgtggcatcgggagctatctaccct
tacaaagcagccaaaggcacctgcaagaccaatggcgtgcccaattcagcttatattactggttatgcacgtgtgccgaggaacaacg
aaagcagcatgatgtacgctgtgtcgaaacaaccaataactgttgctgtcgatgccaatgcaaactttcaatattacaagagcggtgtgtt
taacggaccctgtggaactagtctcaatcacgccgtcaccgctataggttacgggcaggatagcaacggaaaaaaatattggatagta
aagaactcatggggtgccagatggggtgaggccggatacatccgtatggcaagagatgtgtcatcgtcatctggaatatgtggaatcg
ccattgattctctctatcccactctagaatcaagggccaatgtcgaagccattaaaatggtttctgaaagtcgaagctcagtgtgcggccg
cgtcgatcg

Fig. 6c atgacttccaaagttcaactcgtgtttcttttcttgtttctctgtgtgatgtgggcttcgccatcggcagcttcttgtgacgaacccagtgatc
ccatgatgaagcagtttgaagaatggatggcggagtacggccgagtttacaaggacaacgacgagaagatgctccggtttcagatatt
caagaacaacgtgaaccatatcgaaacctttaacaatcgcaacggaaattcgtacactctcggtatcaatcaatttaccgatatgacaaa
taacgaatttgttgctcaatatactggtttatctctcccactaaatatcaagagagagccagtggtgtcgtttgatgacgtagacatctcctc
ggtgcctcaaagtattgattggagagactctggtgccgtaacaagtgtcaagaaccaaggccgctgtggttcttgctgggcattcgcgt
caattgcgacggtagaatcaatctacaagatcaaaagagggaacttagtatctttatcggagcagcaagttctcgattgtgctgtaagct
acgggtgcaaaggcggctggataaacaaggcctacagtttcatcatatccaacaagggcgtggcatccgcagctatctacccttacaa
agcagccaaaggtacctgcaagaccaatggcgtgcccaattcagcttatattactcgctatacatatgtgcagaggaacaacgaacgc
aacatgatgtacgctgtgtcgaatcaaccaatagctgctgctctcgatgccagtggaaactttcaacattacaagcgcggtgtgtttacc
ggaccttgtggaactagactcaatcatgccatcgtcattataggttacgggcaggatagcagcggaaaaaaattttggatagtaaggaa
ctcatggggtgccggatggggtgaggtggatacatccgcttggcaagagatgtgtcatcgtcatttggattatgtggaatcgccatgg
accctctctatcccactctacaatcagggcccagtgtcgaagtatttgcggccgc

Fig. 6d atggcttccaaagttcaactcgtgtttctttcttgtttctctgtgcgatgtgggcttcgccatcggcagcttctcgtgacgaacccaatgatc
ccatgatgaagcggtttgaagaatggatggcggagtacggccgagtttacaaggacgacgacgagaagatgcgccggtttcagatat

Fig. 6d (cont.)

tcaagaacaacgtgaagcatatcgaaacctttaacagtcgcaacgaaaattcgtacactctcggtatcaatcagtttaccgatatgacaa
aaagcgaatttgttgctcaatataccggcgtatctctcccactaaatatcgagagagagccagtggtgtcatttgatgacgtaaacatctc
cgcggtgcctcaaagtattgattggagagactatggtgccgtaaacgaggtcaagaatcaaaaccctgtggttcttgctggtcattcg
ctgcaattgcgacggtggagggaatctacaagatcaaaacagggtacttagtatctttatcggagcaagaagttctcgattgtgctgtta
gctacgggtgcaaaggcggctgggtgaacaaggcctacgatttcatcatatctaacaacggtgtgaccaccgaagaaaactatcctta
tctagcataccaaggcacttgcaacgccaatagctttcctaattcagcttacattactggttattcatatgtgcgaaggaacgacgaacgc
agcatgatgtacgctgtgtcgaatcaaccaatagctgctcttatcgatgccagtgaaaactttcaatattacaatggcggtgtgtttagcg
gaccttgtggaactagtctcaatcatgccattaccattataggttacgggcaggatagcagtggaacaaaatattggatagtaaggaact
cgtggggcagctcatggggtgagggtggatacgtccgtatggcaagaggtgtgtcatcgtcatctggagtatgtggaatcgccatgg
ctcctctctttcccactctacaatcaggggctaatgccgaagttattaagatggtttctgaaacttccggccgcagctacgt

Fig. 9

```
                                    351                     384
        Proprotease (O. sativum)  (301) CGIAQMASYPV------------------
     Procathepsin L (H. sapiens)  (301) CGIASAASYPTV-----------------
           Propapain (C. papaya)  (330) CGLYTSSFYPVKN----------------
     Procathepsin L (M. musculus) (322) CGLATAASYPVVN----------------
                  AN1 (A. comosus) (322) CGIAMDPLYPTLQSGPSVEVI--------
                  STB4 (A. comosus) (323) CGIAIDPLYPTLESGANVEAIKMVSESRSSV
                  STB3 (A. comosus) (323) CGIAIDSLYPTLESRANVEAIKMVSESRSSV
        Fruit bromelain (A. comosus) (324) CGIAMDPLYPTLQSGANVAVIKMVSKT----
                  FB1 (A. comosus) (322) CGIAMAPLFPTLQSGANAEVIKMVSET----
        Cysteine protease (V. mungo) (331) CGIAMMASYPIKNSSDNPTGSLSSPKDEL--
```

Fig. 10

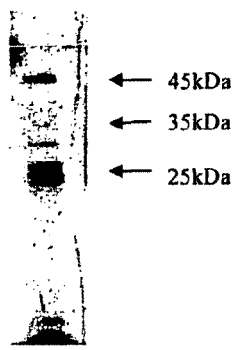

← 45kDa
← 35kDa
← 25kDa

SEQUENCE LISTING

<160> NUMBER OF SEQ ID NOS: 76

<210> SEQ ID NO 1
<211> LENGTH: 359
<212> TYPE: PRT
<213> ORGANISM: Ananas comosus

<400> SEQUENCE: 1

```
Met Ala Trp Lys Val Gln Leu Val Phe Leu Phe Leu Phe Leu Cys Val
1               5                   10                  15

Met Trp Ala Ser Pro Ser Ala Ala Ser Ala Asp Glu Pro Ser Asp Pro
            20                  25                  30

Met Met Lys Arg Phe Glu Glu Trp Met Val Glu Tyr Gly Arg Val Tyr
        35                  40                  45

Lys Asp Asn Asp Glu Lys Met Arg Arg Phe Gln Ile Phe Lys Asn Asn
    50                  55                  60

Val Asn His Ile Glu Thr Phe Asn Ser Arg Asn Lys Asn Ser Tyr Thr
65                  70                  75                  80

Leu Gly Ile Asn Gln Phe Thr Asp Met Thr Asn Asn Glu Phe Val Ala
                85                  90                  95

Gln Tyr Thr Gly Gly Ile Ser Arg Pro Leu Asn Ile Glu Arg Glu Pro
            100                 105                 110

Val Val Ser Phe Asp Asp Val Asp Ile Ser Ala Val Pro Gln Ser Ile
        115                 120                 125

Asp Trp Arg Asp Tyr Gly Ala Val Thr Ser Val Lys Asn Gln Asn Pro
    130                 135                 140

Cys Gly Ala Cys Trp Ala Phe Ala Ala Ile Ala Thr Val Glu Ser Ile
145                 150                 155                 160

Tyr Lys Ile Lys Lys Gly Ile Leu Glu Pro Leu Ser Glu Gln Gln Val
                165                 170                 175
```

-continued

```
Leu Asp Cys Ala Lys Gly Tyr Gly Cys Lys Gly Gly Trp Glu Phe Arg
            180                 185                 190

Ala Phe Glu Phe Ile Ile Ser Asn Lys Gly Val Ala Ser Ala Ala Ile
            195                 200                 205

Tyr Pro Tyr Lys Ala Ala Lys Gly Thr Cys Lys Thr Asn Gly Val Pro
            210                 215                 220

Asn Ser Ala Tyr Ile Thr Gly Tyr Ala Arg Val Pro Arg Asn Asn Glu
225                 230                 235                 240

Ser Ser Met Met Tyr Ala Val Ser Lys Gln Pro Ile Thr Val Ala Val
                245                 250                 255

Asp Ala Asn Ala Asn Phe Gln Tyr Tyr Lys Ser Gly Val Phe Asn Gly
            260                 265                 270

Pro Cys Gly Thr Ser Leu Asn His Ala Val Thr Ala Ile Gly Tyr Gly
            275                 280                 285

Gln Asp Ser Asn Gly Lys Lys Tyr Trp Ile Val Lys Asn Ser Trp Gly
            290                 295                 300

Ala Arg Trp Gly Glu Ala Gly Tyr Ile Arg Met Ala Arg Asp Val Ser
305                 310                 315                 320

Ser Ser Ser Gly Ile Cys Gly Ile Ala Ile Asp Pro Leu Tyr Pro Thr
                325                 330                 335

Leu Glu Ser Gly Ala Asn Val Glu Ala Ile Lys Met Val Ser Glu Ser
            340                 345                 350

Arg Ser Ser Val Cys Gly Arg
            355

<210> SEQ ID NO 2
<211> LENGTH: 361
<212> TYPE: PRT
<213> ORGANISM: Ananas comosus

<400> SEQUENCE: 2

Met Ala Trp Lys Val Gln Val Val Phe Leu Phe Leu Phe Leu Cys Val
1               5                   10                  15

Met Trp Ala Ser Pro Ser Ala Ala Ser Ala Asp Glu Pro Ser Asp Pro
            20                  25                  30

Met Met Lys Arg Phe Glu Glu Trp Met Val Glu Tyr Gly Arg Val Tyr
            35                  40                  45

Lys Asp Asn Asp Glu Lys Met Arg Arg Phe Gln Ile Phe Lys Asn Asn
        50                  55                  60

Val Asn His Ile Glu Thr Phe Asn Ser Arg Asn Glu Asn Ser Tyr Thr
65                  70                  75                  80

Leu Gly Ile Asn Gln Phe Thr Asp Met Thr Asn Asn Glu Phe Ile Ala
                85                  90                  95

Gln Tyr Thr Gly Gly Ile Ser Arg Pro Leu Asn Ile Glu Arg Glu Pro
            100                 105                 110

Val Val Ser Phe Asp Asp Val Asp Ile Ser Ala Val Pro Gln Ser Ile
            115                 120                 125

Asp Trp Arg Asp Tyr Gly Ala Val Thr Ser Val Lys Asn Gln Asn Pro
        130                 135                 140

Cys Gly Ala Cys Trp Ala Phe Ala Ala Ile Ala Thr Val Glu Ser Ile
145                 150                 155                 160

Tyr Lys Ile Lys Lys Gly Ile Leu Glu Pro Leu Ser Glu Gln Gln Val
                165                 170                 175

Leu Asp Cys Ala Lys Gly Tyr Gly Cys Lys Gly Gly Trp Glu Phe Arg
            180                 185                 190
```

```
Ala Phe Glu Phe Ile Ile Ser Asn Lys Gly Val Ala Ser Gly Ala Ile
            195                 200                 205

Tyr Pro Tyr Lys Ala Ala Lys Gly Thr Cys Lys Thr Asn Gly Val Pro
210                 215                 220

Asn Ser Ala Tyr Ile Thr Gly Tyr Ala Arg Val Pro Arg Asn Asn Glu
225                 230                 235                 240

Ser Ser Met Met Tyr Ala Val Ser Lys Gln Pro Ile Thr Val Ala Val
            245                 250                 255

Asp Ala Asn Ala Asn Phe Gln Tyr Tyr Lys Ser Gly Val Phe Asn Gly
            260                 265                 270

Pro Cys Gly Thr Ser Leu Asn His Ala Val Thr Ala Ile Gly Tyr Gly
            275                 280                 285

Gln Asp Ser Asn Gly Lys Lys Tyr Trp Ile Val Lys Asn Ser Trp Gly
            290                 295                 300

Ala Arg Trp Gly Glu Ala Gly Tyr Ile Arg Met Ala Arg Asp Val Ser
305                 310                 315                 320

Ser Ser Ser Gly Ile Cys Gly Ile Ala Ile Asp Ser Leu Tyr Pro Thr
                325                 330                 335

Leu Glu Ser Arg Ala Asn Val Glu Ala Ile Lys Met Val Ser Glu Ser
            340                 345                 350

Arg Ser Ser Val Cys Gly Arg Val Asp
            355                 360

<210> SEQ ID NO 3
<211> LENGTH: 345
<212> TYPE: PRT
<213> ORGANISM: Ananas comosus

<400> SEQUENCE: 3

Met Thr Ser Lys Val Gln Leu Val Phe Leu Phe Leu Phe Leu Cys Val
1               5                  10                  15

Met Trp Ala Ser Pro Ser Ala Ala Ser Cys Asp Glu Pro Ser Asp Pro
            20                  25                  30

Met Met Lys Gln Phe Glu Glu Trp Met Ala Glu Tyr Gly Arg Val Tyr
        35                  40                  45

Lys Asp Asn Asp Glu Lys Met Leu Arg Phe Gln Ile Phe Lys Asn Asn
50                  55                  60

Val Asn His Ile Glu Thr Phe Asn Asn Arg Asn Gly Asn Ser Tyr Thr
65                  70                  75                  80

Leu Gly Ile Asn Gln Phe Thr Asp Met Thr Asn Asn Glu Phe Val Ala
            85                  90                  95

Gln Tyr Thr Gly Leu Ser Leu Pro Leu Asn Ile Lys Arg Glu Pro Val
        100                 105                 110

Val Ser Phe Asp Asp Val Asp Ile Ser Ser Val Pro Gln Ser Ile Asp
    115                 120                 125

Trp Arg Asp Ser Gly Ala Val Thr Ser Val Lys Asn Gln Gly Arg Cys
130                 135                 140

Gly Ser Cys Trp Ala Phe Ala Ser Ile Ala Thr Val Glu Ser Ile Tyr
145                 150                 155                 160

Lys Ile Lys Arg Gly Asn Leu Val Ser Leu Ser Glu Gln Gln Val Leu
            165                 170                 175

Asp Cys Ala Val Ser Tyr Gly Cys Lys Gly Gly Trp Ile Asn Lys Ala
        180                 185                 190

Tyr Ser Phe Ile Ile Ser Asn Lys Gly Val Ala Ser Ala Ala Ile Tyr
    195                 200                 205
```

```
Pro Tyr Lys Ala Ala Lys Gly Thr Cys Lys Thr Asn Gly Val Pro Asn
    210                 215                 220
Ser Ala Tyr Ile Thr Arg Tyr Thr Tyr Val Gln Arg Asn Asn Glu Arg
225                 230                 235                 240
Asn Met Met Tyr Ala Val Ser Asn Gln Pro Ile Ala Ala Ala Leu Asp
                245                 250                 255
Ala Ser Gly Asn Phe Gln His Tyr Lys Arg Gly Val Phe Thr Gly Pro
                260                 265                 270
Cys Gly Thr Arg Leu Asn His Ala Ile Val Ile Gly Tyr Gly Gln
                275                 280                 285
Asp Ser Ser Gly Lys Lys Phe Trp Ile Val Arg Asn Ser Trp Gly Ala
    290                 295                 300
Gly Trp Gly Glu Gly Gly Tyr Ile Arg Leu Ala Arg Asp Val Ser Ser
305                 310                 315                 320
Ser Phe Gly Leu Cys Gly Ile Ala Met Asp Pro Leu Tyr Pro Thr Leu
                325                 330                 335
Gln Ser Gly Pro Ser Val Glu Val Ile
                340                 345

<210> SEQ ID NO 4
<211> LENGTH: 356
<212> TYPE: PRT
<213> ORGANISM: Ananas comosus

<400> SEQUENCE: 4

Met Ala Ser Lys Val Gln Leu Val Phe Leu Phe Leu Phe Leu Cys Ala
1               5                   10                  15
Met Trp Ala Ser Pro Ser Ala Ala Ser Arg Asp Glu Pro Asn Asp Pro
            20                  25                  30
Met Met Lys Arg Phe Glu Glu Trp Met Ala Glu Tyr Gly Arg Val Tyr
        35                  40                  45
Lys Asp Asp Asp Glu Lys Met Arg Arg Phe Gln Ile Phe Lys Asn Asn
    50                  55                  60
Val Lys His Ile Glu Thr Phe Asn Ser Arg Asn Glu Asn Ser Tyr Thr
65                  70                  75                  80
Leu Gly Ile Asn Gln Phe Thr Asp Met Thr Lys Ser Glu Phe Val Ala
                85                  90                  95
Gln Tyr Thr Gly Val Ser Leu Pro Leu Asn Ile Glu Arg Glu Pro Val
                100                 105                 110
Val Ser Phe Asp Asp Val Asn Ile Ser Ala Val Pro Gln Ser Ile Asp
                115                 120                 125
Trp Arg Asp Tyr Gly Ala Val Asn Glu Val Lys Asn Gln Asn Pro Cys
    130                 135                 140
Gly Ser Cys Trp Ser Phe Ala Ala Ile Ala Thr Val Glu Gly Ile Tyr
145                 150                 155                 160
Lys Ile Lys Thr Gly Tyr Leu Val Ser Leu Ser Glu Gln Glu Val Leu
                165                 170                 175
Asp Cys Ala Val Ser Tyr Gly Cys Lys Gly Gly Trp Val Asn Lys Ala
                180                 185                 190
Tyr Asp Phe Ile Ile Ser Asn Asn Gly Val Thr Thr Glu Glu Asn Tyr
                195                 200                 205
Pro Tyr Leu Ala Tyr Gln Gly Thr Cys Asn Ala Asn Ser Phe Pro Asn
    210                 215                 220
Ser Ala Tyr Ile Thr Gly Tyr Ser Tyr Val Arg Arg Asn Asp Glu Arg
225                 230                 235                 240
```

Ser Met Met Tyr Ala Val Ser Asn Gln Pro Ile Ala Ala Leu Ile Asp
                245                 250                 255

Ala Ser Glu Asn Phe Gln Tyr Tyr Asn Gly Gly Val Phe Ser Gly Pro
            260                 265                 270

Cys Gly Thr Ser Leu Asn His Ala Ile Thr Ile Ile Gly Tyr Gly Gln
        275                 280                 285

Asp Ser Ser Gly Thr Lys Tyr Trp Ile Val Arg Asn Ser Trp Gly Ser
    290                 295                 300

Ser Trp Gly Glu Gly Gly Tyr Val Arg Met Ala Arg Gly Val Ser Ser
305                 310                 315                 320

Ser Ser Gly Val Cys Gly Ile Ala Met Ala Pro Leu Phe Pro Thr Leu
                325                 330                 335

Gln Ser Gly Ala Asn Ala Glu Val Ile Lys Met Val Ser Glu Thr Ser
            340                 345                 350

Gly Arg Ser Tyr
        355

<210> SEQ ID NO 5
<211> LENGTH: 1081
<212> TYPE: DNA
<213> ORGANISM: Ananas comosus

<400> SEQUENCE: 5
atggcttgga aagttcaact cgtgtttctt ttcttgtttc tctgtgtgat gtgggcttcg     60
ccatcggcag cttctgctga cgaacccagt gatcccatga tgaagcggtt tgaagaatgg    120
atggtggagt acggccgagt ttacaaggac aacgatgaga agatgcgccg gtttcagata    180
ttcaagaaca acgtgaacca tatcgaaacc tttaacagtc gcaataaaaa ttcgtacact    240
ctcggcatca atcagtttac cgatatgaca aataacgaat tgttgctcca atatactggt    300
ggtatatctc gcccactaaa tatcgagaga gagccagtgg tgtcgtttga tgacgtagac    360
atctccgcgg tgcctcaaag tattgattgg agagactacg gtgccgtaac aagtgtcaag    420
aaccaaaacc cctgtggtgc ttgctgggca ttcgctgcaa ttgcgacggt agaatcaatc    480
tacaagatca aaaagggat cttagaacct ttatcggagc agcaagttct cgattgtgct    540
aaaggctacg ggtgcaaagg cggctgggag ttcagggcct tcgaattat catatctaac    600
aagggcgtgg catcggcagc tatctacccct tacaaagcag ccaaaggcac ctgcaagacc    660
aatggcgtgc ccaattcagc ttatattact ggttatgcac gtgtgccgag gaacaacgaa    720
agcagcatga tgtacgctgt gtcgaaacaa ccaataactg ttgctgtcga tgccaatgca    780
aactttcaat attacaagag cggtgtgttt aacgggacct gtggaactag tctcaatca    840
cgctgtcacc gctataggtt acgggcagga tagcaackga waaaaatatt ggatagtaaa    900
gaactcatgg ggtgccagat ggggtgaggc cggatacatc cgtatggcaa agatgtgtc    960
atcgtcatct ggaatatgtg gaatcgccat tgatcctctc tatcccactc tagaatcagg   1020
ggccaatgtc gaagccatta aaatggtttc tgaaagtcga agctcagtgg cggccgcgta   1080
a                                                                  1081

<210> SEQ ID NO 6
<211> LENGTH: 1085
<212> TYPE: DNA
<213> ORGANISM: Ananas comosus

<400> SEQUENCE: 6
atggcttgga aagttcaagt cgtgtttctt ttcttgtttc tctgtgtgat gtgggcttcg     60

```
ccatcggcag cttctgctga cgaacccagt gatcccatga tgaagcggtt tgaagaatgg      120
atggtggagt acggccgagt ttacaaggac aacgatgaga agatgcgccg gtttcagata      180
ttcaagaaca acgtgaacca tatcgaaact tttaacagtc gcaacgaaaa ttcgtacact      240
ctcggcatca atcagtttac cgatatgaca aataacgaat ttattgctca atatactggt      300
ggtatatctc gcccactaaa tatcgagaga gagccagtgg tgtcgtttga tgacgtagac      360
atctccgcgg tgcctcaaag tattgattgg agagactacg gtgccgtaac aagtgtcaag      420
aaccaaaacc cctgtggtgc ttgctgggca ttcgctgcaa ttgcgacggt agaatcaatc      480
tacaagatca aaaagggat cttagaacct ttatcggagc agcaagttct cgattgtgct      540
aaaggctacg ggtgcaaagg cggctgggag ttcagggcct tcgaattcat catatctaac      600
aagggcgtgg catcgggagc tatctaccct tacaaagcag ccaaaggcac ctgcaagacc      660
aatggcgtgc ccaattcagc ttatattact ggttatgcac gtgtgccgag gaacaacgaa      720
agcagcatga tgtacgctgt gtcgaaacaa ccaataactg ttgctgtcga tgccaatgca      780
aactttcaat attacaagag cggtgtgttt aacggaccct gtggaactag tctcaatcac      840
gccgtcaccg ctataggtta cgggcaggat agcaacggaa aaaatattg atagtaaag       900 aactcatggg gtgccagatg gggtgaggcc ggatacatcc gtatggcaag agatgtgtca      960
tcgtcatctg gaatatgtgg aatcgccatt gattctctct atcccactct agaatcaagg     1020
gccaatgtcg aagccattaa aatggtttct gaaagtcgaa gctcagtgtg cggccgcgtc     1080
gatcg                                                                 1085

<210> SEQ ID NO 7
<211> LENGTH: 1043
<212> TYPE: DNA
<213> ORGANISM: Ananas comosus

<400> SEQUENCE: 7
atgacttcca aagttcaact cgtgtttctt ttcttgtttc tctgtgtgat gtgggcttcg       60
ccatcggcag cttcttgtga cgaacccagt gatcccatga tgaagcagtt tgaagaatgg      120
atggcggagt acggccgagt ttacaaggac aacgacgaga agatgctccg gtttcagata      180
ttcaagaaca acgtgaacca tatcgaaacc tttaacaatc gcaacggaaa ttcgtacact      240
ctcggtatca atcaatttac cgatatgaca aataacgaat ttgttgctca atatactggt      300
ttatctctcc cactaaatat caagagagag ccagtggtgt cgtttgatga cgtagacatc      360
tcctcggtgc ctcaaagtat tgattggaga gactctggtg ccgtaacaag tgtcaagaac      420
caaggccgct gtggttcttg ctgggcattc gcgtcaattg cgacggtaga atcaatctac      480
aagatcaaaa gagggaactt agtatcttta tcggagcagc aagttctcga ttgtgctgta      540
agctacgggt gcaaaggcgg ctggataaac aaggcctaca gtttcatcat atccaacaag      600
ggcgtggcat ccgcagctat ctacccttac aaagcagcca aggtacctg caagaccaat       660 ggcgtgccca attcagctta tattactcgc tatacatatg tgcagaggaa caacgaacgc      720
aacatgatgt acgctgtgtc gaatcaacca atagctgctg ctctcgatgc cagtggaaac      780
tttcaacatt acaagcgcgg tgtgtttacc ggaccttgtg gaactagact caatcatgcc      840
atcgtcatta taggttacgg gcaggatagc agcggaaaaa atttggat agtaaggaac       900 tcatggggtg ccggatgggg tgagggtgga tacatccgct ggcaagaga tgtgtcatcg      960 tcatttggat tatgtggaat cgccatggac cctctctatc ccactctaca atcagggccc     1020
agtgtcgaag tatttgcggc cgc                                             1043
```

<210> SEQ ID NO 8
<211> LENGTH: 1070
<212> TYPE: DNA
<213> ORGANISM: Ananas comosus

<400> SEQUENCE: 8

| | | | | | |
|---|---|---|---|---|---|
| atggcttcca | aagttcaact | cgtgtttctt | ttcttgtttc | tctgtgcgat | gtgggcttcg | 60 |
| ccatcggcag | cttctcgtga | cgaacccaat | gatcccatga | tgaagcggtt | tgaagaatgg | 120 |
| atggcggagt | acggccgagt | ttacaaggac | gacgacgaga | agatgcgccg | gtttcagata | 180 |
| ttcaagaaca | acgtgaagca | tatcgaaacc | tttaacagtc | gcaacgaaaa | ttcgtacact | 240 |
| ctcggtatca | atcagtttac | cgatatgaca | aaaagcgaat | tgttgctca | atataccggc | 300 |
| gtatctctcc | cactaaatat | cgagagagag | ccagtggtgt | catttgatga | cgtaaacatc | 360 |
| tccgcggtgc | ctcaaagtat | tgattggaga | gactatggtg | ccgtaaacga | ggtcaagaat | 420 |
| caaaccccct | gtggttcttg | ctggtcattc | gctgcaattg | cgacggtgga | gggaatctac | 480 |
| aagatcaaaa | cagggtactt | agtatcttta | tcggagcaag | aagttctcga | ttgtgctgtt | 540 |
| agctacgggt | gcaaaggcgg | ctgggtgaac | aaggcctacg | atttcatcat | atctaacaac | 600 |
| ggtgtgacca | ccgaagaaaa | ctatccttat | ctagcatacc | aaggcacttg | caacgccaat | 660 |
| agctttccta | attcagctta | cattactggt | tattcatatg | tgcgaaggaa | cgacgaacgc | 720 |
| agcatgatgt | acgctgtgtc | gaatcaacca | atagctgctc | ttatcgatgc | cagtgaaaac | 780 |
| tttcaatatt | acaatggcgg | tgtgtttagc | ggaccttgtg | gaactagtct | caatcatgcc | 840 |
| attaccatta | taggttacgg | gcaggatagc | agtggaacaa | aatattggat | agtaaggaac | 900 |
| tcgtggggca | gctcatgggg | tgaggtggga | tacgtccgta | tggcaagagg | tgtgtcatcg | 960 |
| tcatctggag | tatgtggaat | cgccatggct | cctctctttc | ccactctaca | atcaggggct | 1020 |
| aatgccgaag | ttattaagat | ggtttctgaa | acttccggcc | gcagctacgt | | 1070 |

<210> SEQ ID NO 9
<211> LENGTH: 29
<212> TYPE: DNA
<213> ORGANISM: Artificial Sequence
<220> FEATURE:
<223> OTHER INFORMATION: Cysprot_c_down
<220> FEATURE:
<221> NAME/KEY: misc_feature
<222> LOCATION: (21)..(21)
<223> OTHER INFORMATION: n is a, c, g, or t

<400> SEQUENCE: 9
ccgtagccga tgatggtgay ngcrtgrtt                                     29

<210> SEQ ID NO 10
<211> LENGTH: 26
<212> TYPE: DNA
<213> ORGANISM: Artificial Sequence
<220> FEATURE:
<223> OTHER INFORMATION: Cysprot_d_down
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 10
ccnggnacrc cgtggaggga cttggt                                        26

<210> SEQ ID NO 11
<211> LENGTH: 26
<212> TYPE: DNA
<213> ORGANISM: Artificial Sequence
<220> FEATURE:
<223> OTHER INFORMATION: Cysprot_1_up
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 11
ccnggnacrc cgtggaggga cttggt                                        26

<210> SEQ ID NO 12
<211> LENGTH: 29
<212> TYPE: DNA
<213> ORGANISM: Artificial Sequence
<220> FEATURE:
<223> OTHER INFORMATION: Cysprot_3_up

<400> SEQUENCE: 12
gccaccgtgg agtccatcta yaarathaa                                     29

<210> SEQ ID NO 13
<211> LENGTH: 24
<212> TYPE: DNA
<213> ORGANISM: Artificial Sequence
<220> FEATURE:
<223> OTHER INFORMATION: Cysprot_a_down
<220> FEATURE:
<221> NAME/KEY: misc_feature
<222> LOCATION: (19)..(19)
<223> OTHER INFORMATION: n is a, c, g, or t

<400> SEQUENCE: 13
cagcgggtcc atggcdatnc crca                                          24

<210> SEQ ID NO 14
<211> LENGTH: 24
<212> TYPE: DNA
<213> ORGANISM: Artificial Sequence
<220> FEATURE:
<223> OTHER INFORMATION: Cysprot_b_down

<400> SEQUENCE: 14
gaacacgccg cgcttrtart rytg                                          24

<210> SEQ ID NO 15
<211> LENGTH: 5
<212> TYPE: PRT
<213> ORGANISM: Ananas comosus

<400> SEQUENCE: 15

Tyr Trp Ile Val Lys
1               5

<210> SEQ ID NO 16
<211> LENGTH: 24
<212> TYPE: PRT
<213> ORGANISM: Ananas comosus

<400> SEQUENCE: 16

```
Asn Gln Asn Pro Cys Gly Ala Cys Trp Ala Phe Ala Ala Ile Ala Thr
1               5                   10                  15

Val Glu Ser Ile Tyr Lys Ile Lys
            20

<210> SEQ ID NO 17
<211> LENGTH: 6
<212> TYPE: PRT
<213> ORGANISM: Ananas comosus

<400> SEQUENCE: 17

Gly Gly Trp Glu Phe Arg
1               5

<210> SEQ ID NO 18
<211> LENGTH: 9
<212> TYPE: PRT
<213> ORGANISM: Ananas comosus

<400> SEQUENCE: 18

Ala Phe Glu Phe Ile Ile Ser Asn Lys
1               5

<210> SEQ ID NO 19
<211> LENGTH: 5
<212> TYPE: PRT
<213> ORGANISM: Ananas comosus

<400> SEQUENCE: 19

Tyr Trp Ile Val Lys
1               5

<210> SEQ ID NO 20
<211> LENGTH: 24
<212> TYPE: PRT
<213> ORGANISM: Ananas comosus

<400> SEQUENCE: 20

Asn Gln Asn Pro Cys Gly Ala Cys Trp Ala Phe Ala Ala Ile Ala Thr
1               5                   10                  15

Val Glu Ser Ile Tyr Lys Ile Lys
            20

<210> SEQ ID NO 21
<211> LENGTH: 6
<212> TYPE: PRT
<213> ORGANISM: Ananas comosus

<400> SEQUENCE: 21

Gly Gly Trp Glu Phe Arg
1               5

<210> SEQ ID NO 22
<211> LENGTH: 9
<212> TYPE: PRT
<213> ORGANISM: Ananas comosus

<400> SEQUENCE: 22

Ala Phe Glu Phe Ile Ile Ser Asn Lys
1               5

<210> SEQ ID NO 23
<211> LENGTH: 5
<212> TYPE: PRT
<213> ORGANISM: Ananas comosus
```

<400> SEQUENCE: 23

Tyr Trp Ile Val Lys
1               5

<210> SEQ ID NO 24
<211> LENGTH: 24
<212> TYPE: PRT
<213> ORGANISM: Ananas comosus

<400> SEQUENCE: 24

Asn Gln Asn Pro Cys Gly Ala Cys Trp Ala Phe Ala Ala Ile Ala Thr
1               5                   10                  15

Val Glu Ser Ile Tyr Lys Ile Lys
            20

<210> SEQ ID NO 25
<211> LENGTH: 6
<212> TYPE: PRT
<213> ORGANISM: Ananas comosus

<400> SEQUENCE: 25

Gly Gly Trp Glu Phe Arg
1               5

<210> SEQ ID NO 26
<211> LENGTH: 9
<212> TYPE: PRT
<213> ORGANISM: Ananas comosus

<400> SEQUENCE: 26

Ala Phe Glu Phe Ile Ile Ser Asn Lys
1               5

<210> SEQ ID NO 27
<211> LENGTH: 4
<212> TYPE: PRT
<213> ORGANISM: Ananas comosus

<400> SEQUENCE: 27

Ile Ile Tyr Pro
1

<210> SEQ ID NO 28
<211> LENGTH: 24
<212> TYPE: PRT
<213> ORGANISM: Ananas comosus

<400> SEQUENCE: 28

Asn Gln Asn Pro Cys Gly Ala Cys Trp Ala Phe Ala Ala Ile Ala Thr
1               5                   10                  15

Val Glu Ser Ile Tyr Lys Ile Lys
            20

<210> SEQ ID NO 29
<211> LENGTH: 6
<212> TYPE: PRT
<213> ORGANISM: Ananas comosus

<400> SEQUENCE: 29

Gly Gly Trp Glu Phe Arg
1               5

<210> SEQ ID NO 30

```
<211> LENGTH: 9
<212> TYPE: PRT
<213> ORGANISM: Ananas comosus

<400> SEQUENCE: 30

Ala Phe Glu Phe Ile Ile Ser Asn Lys
1               5

<210> SEQ ID NO 31
<211> LENGTH: 5
<212> TYPE: PRT
<213> ORGANISM: Ananas comosus

<400> SEQUENCE: 31

Phe Trp Ile Val Arg
1               5

<210> SEQ ID NO 32
<211> LENGTH: 24
<212> TYPE: PRT
<213> ORGANISM: Ananas comosus

<400> SEQUENCE: 32

Asn Gln Gly Arg Cys Gly Ser Cys Trp Ala Phe Ala Ser Ile Ala Thr
1               5                   10                  15

Val Glu Ser Ile Tyr Lys Ile Lys
            20

<210> SEQ ID NO 33
<211> LENGTH: 6
<212> TYPE: PRT
<213> ORGANISM: Ananas comosus

<400> SEQUENCE: 33

Gly Gly Trp Ile Asn Lys
1               5

<210> SEQ ID NO 34
<211> LENGTH: 9
<212> TYPE: PRT
<213> ORGANISM: Ananas comosus

<400> SEQUENCE: 34

Ala Tyr Ser Phe Ile Ile Ser Asn Lys
1               5

<210> SEQ ID NO 35
<211> LENGTH: 5
<212> TYPE: PRT
<213> ORGANISM: Ananas comosus

<400> SEQUENCE: 35

Phe Trp Ile Val Arg
1               5

<210> SEQ ID NO 36
<211> LENGTH: 24
<212> TYPE: PRT
<213> ORGANISM: Ananas comosus

<400> SEQUENCE: 36

Asn His Ile Pro Cys Gly Ser Cys Trp Ala Phe Ala Ala Ile Ala Thr
1               5                   10                  15

Val Glu Ser Ile Tyr Lys Ile Lys
            20
```

<210> SEQ ID NO 37
<211> LENGTH: 6
<212> TYPE: PRT
<213> ORGANISM: Ananas comosus

<400> SEQUENCE: 37

Gly Gly Trp Val Asn Lys
1               5

<210> SEQ ID NO 38
<211> LENGTH: 9
<212> TYPE: PRT
<213> ORGANISM: Ananas comosus

<400> SEQUENCE: 38

Ala Tyr Asp Phe Ile Ile Ser Asn Lys
1               5

<210> SEQ ID NO 39
<211> LENGTH: 5
<212> TYPE: PRT
<213> ORGANISM: Ananas comosus

<400> SEQUENCE: 39

Tyr Trp Ile Val Lys
1               5

<210> SEQ ID NO 40
<211> LENGTH: 24
<212> TYPE: PRT
<213> ORGANISM: Ananas comosus

<400> SEQUENCE: 40

Asp Gln Asn Pro Cys Gly Ser Cys Trp Ala Phe Ser Ala Ile Ala Thr
1               5                   10                  15

Val Glu Gly Ile Tyr Lys Ile Val
            20

<210> SEQ ID NO 41
<211> LENGTH: 6
<212> TYPE: PRT
<213> ORGANISM: Ananas comosus

<400> SEQUENCE: 41

Gly Gly Phe Val Asp Asn
1               5

<210> SEQ ID NO 42
<211> LENGTH: 9
<212> TYPE: PRT
<213> ORGANISM: Ananas comosus

<400> SEQUENCE: 42

Ala Tyr Asp Phe Ile Ile Ser Asn Asn
1               5

<210> SEQ ID NO 43
<211> LENGTH: 5
<212> TYPE: PRT
<213> ORGANISM: Ananas comosus

<400> SEQUENCE: 43

Tyr Trp Ile Val Lys
1               5

<210> SEQ ID NO 44
<211> LENGTH: 24
<212> TYPE: PRT
<213> ORGANISM: Ananas comosus

<400> SEQUENCE: 44

Asp Gln Asn Pro Cys Gly Ser Cys Trp Ala Phe Ser Ala Ile Ala Thr
1               5                   10                  15

Val Glu Gly Ile Tyr Lys Ile Val
            20

<210> SEQ ID NO 45
<211> LENGTH: 6
<212> TYPE: PRT
<213> ORGANISM: Ananas comosus

<400> SEQUENCE: 45

Gly Gly Phe Val Asp Asn
1               5

<210> SEQ ID NO 46
<211> LENGTH: 9
<212> TYPE: PRT
<213> ORGANISM: Ananas comosus

<400> SEQUENCE: 46

Ala Tyr Asp Phe Ile Ile Ser Asn Asn
1               5

<210> SEQ ID NO 47
<211> LENGTH: 5
<212> TYPE: PRT
<213> ORGANISM: Ananas comosus

<400> SEQUENCE: 47

Tyr Trp Ile Val Lys
1               5

<210> SEQ ID NO 48
<211> LENGTH: 24
<212> TYPE: PRT
<213> ORGANISM: Ananas comosus

<400> SEQUENCE: 48

Asp Gln Asn Pro Cys Gly Ser Cys Trp Ala Phe Ser Ala Ile Ala Thr
1               5                   10                  15

Val Glu Gly Ile Tyr Lys Ile Val
            20

<210> SEQ ID NO 49
<211> LENGTH: 6
<212> TYPE: PRT
<213> ORGANISM: Ananas comosus

<400> SEQUENCE: 49

Gly Gly Phe Val Asp Asn
1               5

<210> SEQ ID NO 50
<211> LENGTH: 9
<212> TYPE: PRT
<213> ORGANISM: Ananas comosus

<400> SEQUENCE: 50

```
Ala Tyr Asp Phe Ile Ile Ser Asn Asn
1               5

<210> SEQ ID NO 51
<211> LENGTH: 5
<212> TYPE: PRT
<213> ORGANISM: Ananas comosus

<400> SEQUENCE: 51

Tyr Trp Ile Val Lys
1               5

<210> SEQ ID NO 52
<211> LENGTH: 24
<212> TYPE: PRT
<213> ORGANISM: Ananas comosus

<400> SEQUENCE: 52

Asp Gln Asn Pro Cys Gly Ser Cys Trp Ala Phe Ser Ala Ile Ala Thr
1               5                   10                  15

Val Glu Gly Ile Tyr Lys Ile Val
            20

<210> SEQ ID NO 53
<211> LENGTH: 6
<212> TYPE: PRT
<213> ORGANISM: Ananas comosus

<400> SEQUENCE: 53

Gly Gly Phe Val Asp Asn
1               5

<210> SEQ ID NO 54
<211> LENGTH: 9
<212> TYPE: PRT
<213> ORGANISM: Ananas comosus

<400> SEQUENCE: 54

Ala Tyr Asp Phe Ile Ile Ser Asn Asn
1               5

<210> SEQ ID NO 55
<211> LENGTH: 5
<212> TYPE: PRT
<213> ORGANISM: Ananas comosus

<400> SEQUENCE: 55

Tyr Trp Ile Val Arg
1               5

<210> SEQ ID NO 56
<211> LENGTH: 24
<212> TYPE: PRT
<213> ORGANISM: Ananas comosus

<400> SEQUENCE: 56

Asn Gln Asn Pro Cys Gly Ser Cys Trp Ala Phe Ala Ala Ile Ala Thr
1               5                   10                  15

Val Glu Gly Ile Tyr Lys Ile Lys
            20

<210> SEQ ID NO 57
<211> LENGTH: 6
<212> TYPE: PRT
```

```
<213> ORGANISM: Ananas comosus

<400> SEQUENCE: 57

Gly Gly Trp Val Asn Lys
1               5

<210> SEQ ID NO 58
<211> LENGTH: 9
<212> TYPE: PRT
<213> ORGANISM: Ananas comosus

<400> SEQUENCE: 58

Ala Tyr Asp Phe Ile Ile Ser Asn Asn
1               5

<210> SEQ ID NO 59
<211> LENGTH: 5
<212> TYPE: PRT
<213> ORGANISM: Ananas comosus

<400> SEQUENCE: 59

Tyr Trp Ile Val Arg
1               5

<210> SEQ ID NO 60
<211> LENGTH: 24
<212> TYPE: PRT
<213> ORGANISM: Ananas comosus

<400> SEQUENCE: 60

Asn Gln Asn Pro Cys Gly Ser Cys Trp Ser Phe Ala Ala Ile Ala Thr
1               5                   10                  15

Val Glu Gly Ile Tyr Lys Ile Lys
            20

<210> SEQ ID NO 61
<211> LENGTH: 6
<212> TYPE: PRT
<213> ORGANISM: Ananas comosus

<400> SEQUENCE: 61

Gly Gly Trp Val Asn Lys
1               5

<210> SEQ ID NO 62
<211> LENGTH: 9
<212> TYPE: PRT
<213> ORGANISM: Ananas comosus

<400> SEQUENCE: 62

Ala Tyr Asp Phe Ile Ile Ser Asn Asn
1               5

<210> SEQ ID NO 63
<211> LENGTH: 5
<212> TYPE: PRT
<213> ORGANISM: Ananas comosus

<400> SEQUENCE: 63

Tyr Trp Ile Val Arg
1               5

<210> SEQ ID NO 64
<211> LENGTH: 24
<212> TYPE: PRT
```

```
<213> ORGANISM: Ananas comosus

<400> SEQUENCE: 64

Asn Gln Asn Pro Cys Gly Ser Cys Trp Ser Phe Ala Ala Ile Ala Thr
1               5                   10                  15

Val Glu Gly Ile Tyr Lys Ile Lys
            20

<210> SEQ ID NO 65
<211> LENGTH: 6
<212> TYPE: PRT
<213> ORGANISM: Ananas comosus

<400> SEQUENCE: 65

Gly Gly Trp Val Asn Lys
1               5

<210> SEQ ID NO 66
<211> LENGTH: 9
<212> TYPE: PRT
<213> ORGANISM: Ananas comosus

<400> SEQUENCE: 66

Ala Tyr Asp Phe Ile Ile Ser Asn Asn
1               5

<210> SEQ ID NO 67
<211> LENGTH: 11
<212> TYPE: PRT
<213> ORGANISM: Oryza sativa

<400> SEQUENCE: 67

Cys Gly Ile Ala Gln Met Ala Ser Tyr Pro Val
1               5                   10

<210> SEQ ID NO 68
<211> LENGTH: 12
<212> TYPE: PRT
<213> ORGANISM: Homo sapiens

<400> SEQUENCE: 68

Cys Gly Ile Ala Ser Ala Ala Ser Tyr Pro Thr Val
1               5                   10

<210> SEQ ID NO 69
<211> LENGTH: 13
<212> TYPE: PRT
<213> ORGANISM: Carica papaya

<400> SEQUENCE: 69

Cys Gly Leu Tyr Thr Ser Ser Phe Tyr Pro Val Lys Asn
1               5                   10

<210> SEQ ID NO 70
<211> LENGTH: 13
<212> TYPE: PRT
<213> ORGANISM: Mus musculus

<400> SEQUENCE: 70

Cys Gly Leu Ala Thr Ala Ala Ser Tyr Pro Val Val Asn
1               5                   10

<210> SEQ ID NO 71
<211> LENGTH: 21
<212> TYPE: PRT
```

<213> ORGANISM: Ananas comosus

<400> SEQUENCE: 71

Cys Gly Ile Ala Met Asp Pro Leu Tyr Pro Thr Leu Gln Ser Gly Pro
1               5                   10                  15

Ser Val Glu Val Ile
            20

<210> SEQ ID NO 72
<211> LENGTH: 31
<212> TYPE: PRT
<213> ORGANISM: Ananas comosus

<400> SEQUENCE: 72

Cys Gly Ile Ala Ile Asp Pro Leu Tyr Pro Thr Leu Glu Ser Gly Ala
1               5                   10                  15

Asn Val Glu Ala Ile Lys Met Val Ser Glu Ser Arg Ser Ser Val
            20                  25                  30

<210> SEQ ID NO 73
<211> LENGTH: 31
<212> TYPE: PRT
<213> ORGANISM: Ananas comosus

<400> SEQUENCE: 73

Cys Gly Ile Ala Ile Asp Ser Leu Tyr Pro Thr Leu Glu Ser Arg Ala
1               5                   10                  15

Asn Val Glu Ala Ile Lys Met Val Ser Glu Ser Arg Ser Ser Val
            20                  25                  30

<210> SEQ ID NO 74
<211> LENGTH: 27
<212> TYPE: PRT
<213> ORGANISM: Ananas comosus

<400> SEQUENCE: 74

Cys Gly Ile Ala Met Asp Pro Leu Tyr Pro Thr Leu Gln Ser Gly Ala
1               5                   10                  15

Asn Val Ala Val Ile Lys Met Val Ser Lys Thr
            20                  25

<210> SEQ ID NO 75
<211> LENGTH: 27
<212> TYPE: PRT
<213> ORGANISM: Ananas comosus

<400> SEQUENCE: 75

Cys Gly Ile Ala Met Ala Pro Leu Phe Pro Thr Leu Gln Ser Gly Ala
1               5                   10                  15

Asn Ala Glu Val Ile Lys Met Val Ser Glu Thr
            20                  25

<210> SEQ ID NO 76
<211> LENGTH: 29
<212> TYPE: PRT
<213> ORGANISM: Vigna mungo

<400> SEQUENCE: 76

Cys Gly Ile Ala Met Met Ala Ser Tyr Pro Ile Lys Asn Ser Ser Asp
1               5                   10                  15

Asn Pro Thr Gly Ser Leu Ser Ser Pro Lys Asp Glu Leu
            20                  25

RECOMBINANT PREPARATION OF SELECTED BROMELAIN FRACTIONS

This application is a U.S. National Phase of International Application No. PCT/EP2008/006564 filed Aug. 8, 2008 designating the U.S. and published in English as WO 2009/033536 on Mar. 19, 2009, which claims the benefit of European Application No. 07018125.0. filed Sep. 14, 2007.

The present invention pertains in general to Bromelain and particularly to the different active compounds contained in this complex mixture of proteins. The present invention provides recombinant expressed cysteine proteases, which are found in Bromelain. It has been found that the recombinant expressed proteins have superior effects in terms of treatment of disorders and conditions than Bromelain or its protein fractions from plant extracts.

Bromelain is defined biochemically as crude extract from pineapple stem and pharmacologically as a mixture of cysteine proteases. Its multitude of positive effects arises at least in part from the proteolytic and particularly fibrinolytic properties. Anti-tumor effects of Bromelain are also known dependent from effects different from proteolytic activity and still of unknown mechanism. Bromelain is the collective name for the proteolytic enzymes found in the tissues, particularly stem and fruit, of the plants of the Bromeliaceae family. The most common form of Bromelain is a mixture of various moieties derived from the stem of the pineapple plant (*Ananas comosus*). Stem Bromelain (hereafter called Bromelain) is known to contain at least five proteolytic enzymes but also non-proteolytic enzymes, including an acid phosphatase and a peroxidase; it may also contain amylase and cellulase activity. In addition, various other components are present.

Several positive effects from Bromelain have been described so far comprising edema reducing, hemolytic, fibrinolytic, anti-inflammatory, anti-metastatic and tumor inhibitory properties. Additionally, stimulating effects on the immune system, acceleration of wound healing are also accorded to the beneficial effects of said natural protease cocktail. It has been shown by Mynott T L et al. (J. Immunol., 163:5 (1999) 2568-75) that Bromelain blocks activation of ERK-2 in Th0 cells stimulated via the TCR. Bromelain also inhibited PMA-induced IL-2, IFN-gamma, and IL-4 mRNA accumulation, but had no effect on TCR-induced cytokine mRNA production. This suggests that said complex mixture of proteases is an inhibitor of T-cell signal transduction.

Due to the efficacy of Bromelain after oral administration, its safety and lack of undesired side effects, Bromelain has earned growing acceptance and compliance among patients as a phytotherapeutical drug. A wide range of therapeutic benefits has been claimed for Bromelain, such as reversible inhibition of platelet aggregation, angina pectoris, bronchitis, sinusitis, surgical traumas, thrombophlebitis, pyelonephritis and enhanced absorption of drugs, particularly of antibiotics (cf. Orsini R A, Plast. Reconstr. Surg., 118(7) (2006) 1640-4; Brien S, Evid Based Complement Alternat. Med., 1(3) (2004) 251-7. Biochemical experiments indicate that these pharmacological properties depend on the proteolytic activity only partly, suggesting the presence of non proteinaceous factors in Bromelain. Results from preclinical and pharmacological studies recommend Bromelain as a drug for complementary tumor therapy. It is supposed that Bromelain acts as an immuno modulator by raising the impaired immuno cytotoxicity of monocytes against tumor cells from patients and by inducing the production of distinct cytokines such as tumor necrosis factor and interleukins (cf. Maurer H R, Cell. Mol. Life. Sci., 58(9) (2001), 1234-45). There are also reports on animal experiments, in which an anti-metastatic efficacy and inhibition of metastasis-associated platelet aggregation as well as inhibition of growth and invasiveness of tumor cells is described. Apparently, the anti-invasive activity does not depend on the proteolytic activity. This is also true for Bromelain effects on the modulation of immune functions, its potential to eliminate burn debris and to accelerate wound healing.

A physical extraction process for Bromelain is e.g. disclosed in CN1186118. The process comprises inter alia pretreating pineapple plant by freezing, crushing, squeezing to obtain juice, filter to obtain clear liquid, concentrating by ultrafilter film and reverse osmosizing film and freeze vacuum drying to obtain product in the form of sponge. Controlling of temperature, time and pH value is reported to increase enzyme activity and yields.

U.S. Pat. No. 3,658,651 relates Bromelain-containing juice extracted from pineapple plant stems is purified prior to precipitation of the enzyme by passing the juice in ion exchange relation with an anion exchanger in the bicarbonate form, a cation exchanger having weak acid functional groups, and a second anion exchanger in the bicarbonate form.

U.S. Pat. No. 4,286,064 discloses inter alia the preparation of a Bromelain raw extract. The juice from the pineapple stem is first adjusted to a pH of about 3 or 4 with phosphoric acid, and sodium sulfhydride is added to protect against sulfhydryl oxidation. The inert material is precipitated in e.g. acetone and filtrated. The clarified fluid is precipitated with acetone and the precipitate collected by centrifugation and either redissolved in water containing sodium sulfhydride which has been acidified with phosphoric acid and reprecipitated, or dried in a vacuum oven directly. Further purification of the raw extract may be performed by filtration, dialysis or diafiltration for the removal of small molecules and proteins, followed by concentrating the solution obtained prior to lyophilization.

In order to prevent degradation and/or other undesired chemical reactions, such as oxidation reactions, the selection of particular treatment conditions, such as temperature, pH, solvents and buffers, and/or additives, such as stabilizers and antioxidants, is ineluctable.

Apart from the above shortcomings, a further purification of raw extracts may be required. Such purification may be performed for example via HPLC as outlined in US 2002/188107.

It is therefore highly desirable to provide chemically stable as well as pure Bromelain proteins, which may be included in pharmaceutical, dermatological and nutritional compositions and do not exhibit the above shortcomings of the prior art Bromelain containing formulations.

The above problem has been solved by providing heterologously expressed Bromelain protein or a fragment thereof, wherein said Bromelain protein or fragment thereof has been expressed in substantial amounts in soluble and active form in a heterologous host.

The present inventors have surprisingly found that by heterologous expression of single Bromelain proteins or a fragment thereof also stability problems of the proteins/fragments and composition may be avoided. Without wishing to be bound by any theory it is presently assumed that the multiple proteases contained in Bromelain exert a degrading activity on each other, which is only inhibited in part by the protease inhibitors contained therein, leading to auto-degradation. In addition, it could be shown that single, heterologously expressed proteins and/or fragments thereof exert at least some of the advantageous properties of Bromelain. This renders the present proteins or fragments thereof suitable as active ingredients in medicaments. Another positive effect resides in a more specific mode of action avoiding side effects, which may occur in case the complex mixtures of Bromelain or Bromelain fractions are applied.

IN THE FIGURES, SHOWS

Figures 4A, 4B:
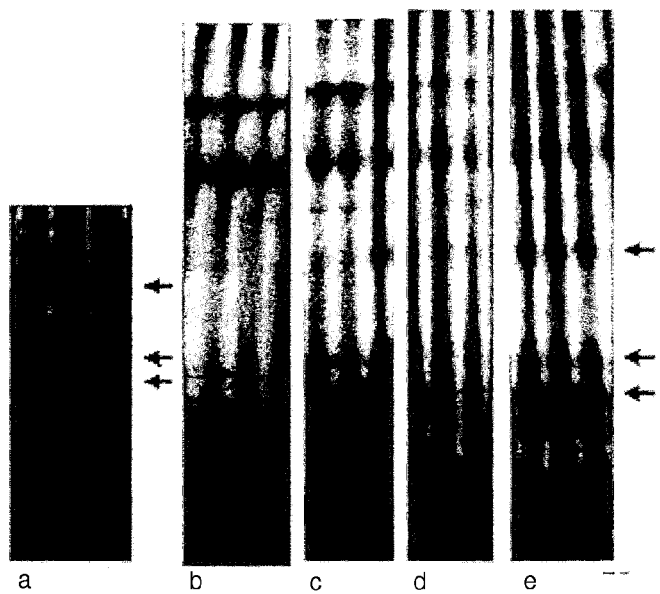
Figure 7:
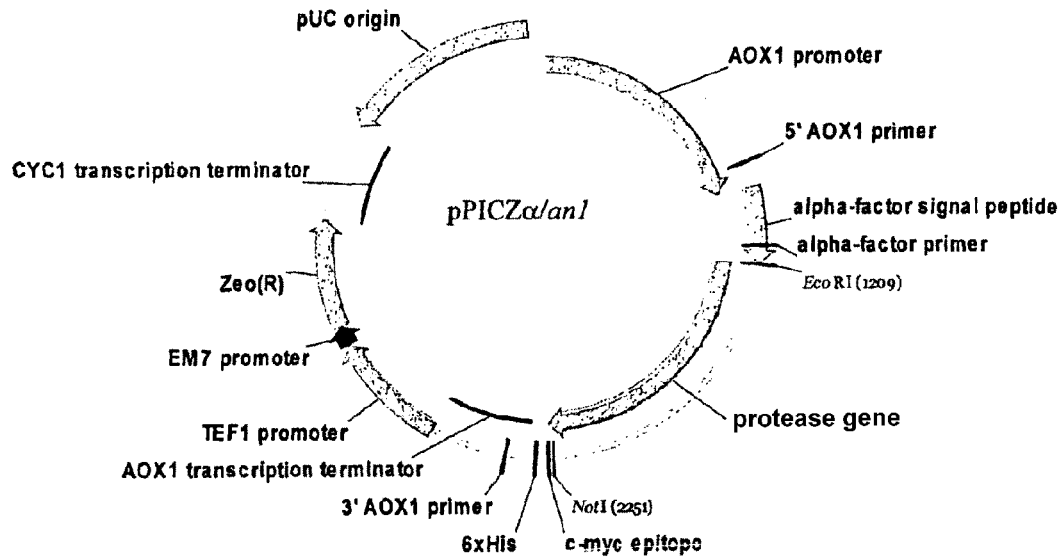
Figure 8:
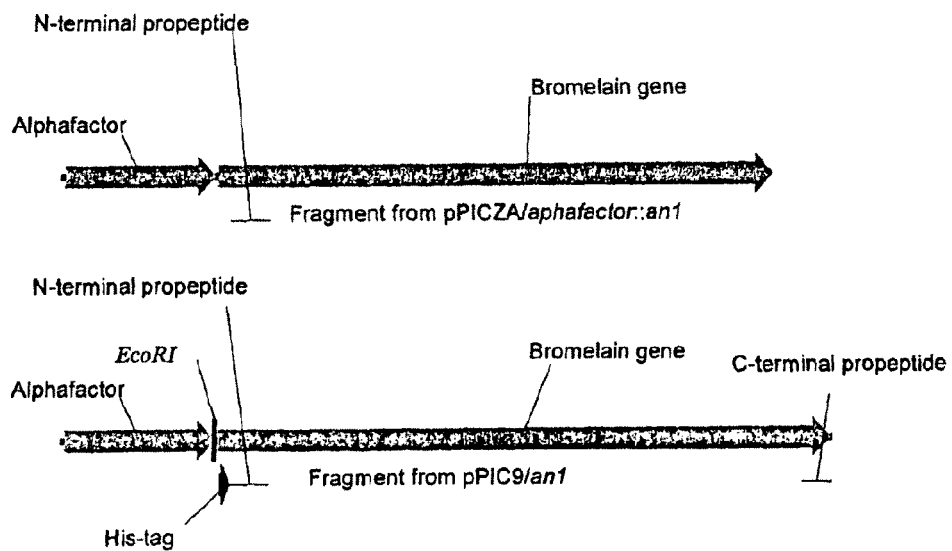
Figure 11:
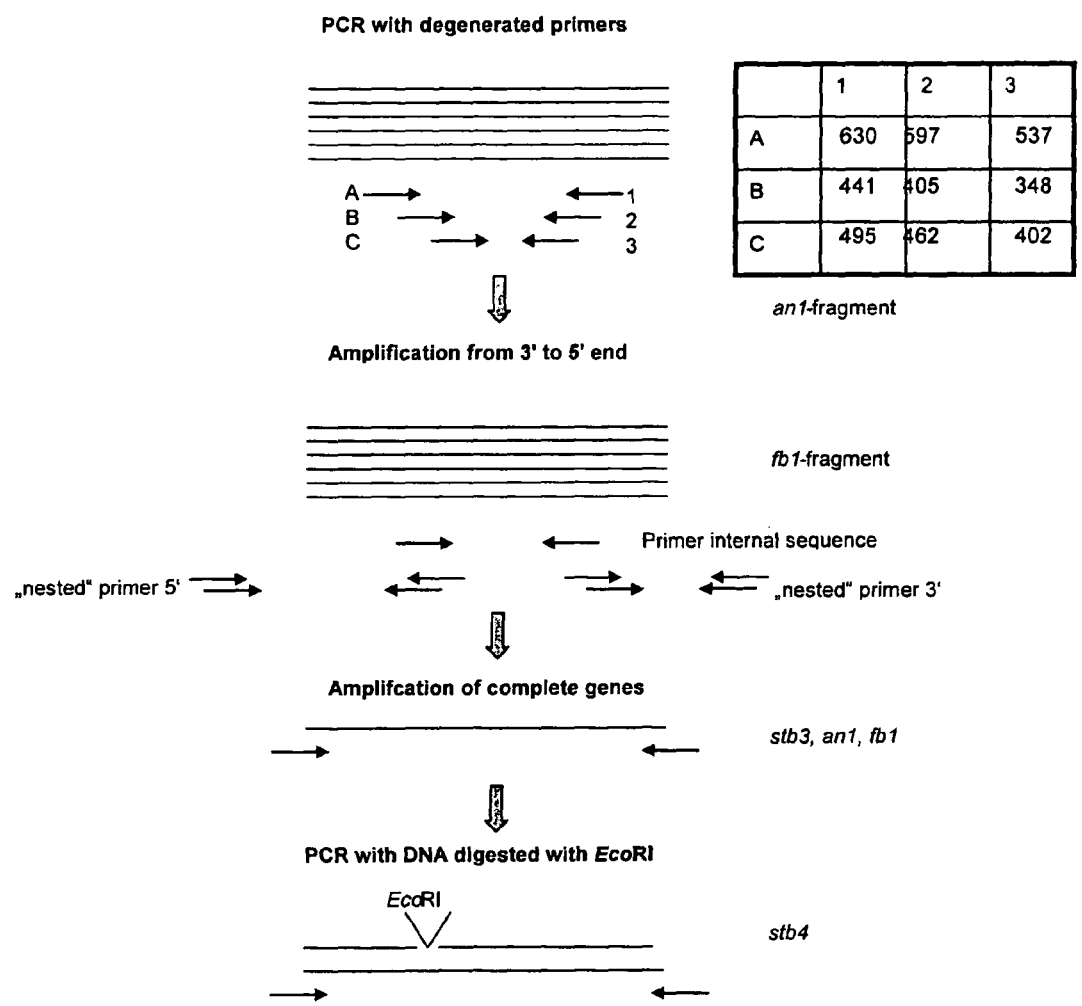

FIG. 1 an alignment performed with the vector NTI program (Invitrogen) employing the Clustal W algorithm (Thompson et al., 1994) of the known cysteine proteases from *A. comosus* and those found by sequencing the peptides of fractions F4, F5 and F9 (underlined) performed according to Harrach and Maurer (1996). Ananain may be found in fraction F9, whereas F4 and F5 comprise stem Bromelain and shows the novel sequence;

FIG. 2 expression of stem Bromelain and Ananain. An SDS-PAGE with approximately 100 µl supernatant from *Pichia pastoris* expression cultures has been conducted. A. positive cysteine proteinase precursor pPIC9/stb3 (stem Bromelain) clones 27 and 30, B negative control (plasmid without insert) and positive pPIC9/anl-clones (Ananain) 4 and 5 as well as positive pPIC9/stb3 clone 30. Arrows mark the heterologously expressed pre-pro-proteins. The right line shows the protein standard (PageRuler™, Fermentas, 10 kDa-170 kDa);

FIG. 3 a 15% SDS-Page of the expression of a pro-Ananain (pPICZ/alpha-factor::anlΔctpp,) construct. The DNA sequence for C-terminal Propeptide was removed. The upper arrow marks the 35 kDa band (proenzyme); down arrow the 25 kDa (active form) band; on the extremely right the wild-type control;

FIG. 4 a 15% SDS-Page of an expression culture with 0,5% casein. FIG. 4 shows a selection of clones with different promoter activities. a) KM71H wild type, b) pPICZ-Δ7/alphafactor::anlΔctpp, b) pPICZ-mini/alphafactor::anlΔctpp. In contrast to FIG. 4a, but for the minimal promoter, the casein signals marked by arrows are not any more detectable with exception of some samples;

FIG. 5 the protein sequences of two stem Bromelains STB4 and STB3 (FIGS. 5a and 5b), Ananain AN1(FIG. 5c) and fruit Bromelain FB1(FIG. 5d);

FIG. 6 the corresponding nucleotide sequences of two stem Bromelains stb4 and stb3 (FIGS. 6a and 6b), Ananain an1 (FIG. 6c) and fruit Bromelain fb1 (FIG. 6d);

FIG. 7 the vector pPICZalpha comprising an1;

FIG. 8 a comparison of expression constructs. The above part of the figure shows the Proananain gene without C-terminal extension within the pPICZA-vector. The below part of the figure illustrate the pPIC9-construct with Preproananain gene and N-terminal His-tag. The C-terminal extension is marked;

FIG. 9 the C-terminal propetide of cysteine proteases. An alignment has been performed using Clustal W available on the world wide web at: ebi.ac.uk), in which the respective C-termini of some of the present cysteine proteases as well as a cysteine protease from rice (AAM34401), human procathepsin L (ICJL Gl:2392232) ICJL), propapain (P00784), murine procathepsin L (P06797), fruit bromelain (BAA21848) and a cysteine protease exhibiting a defined vacuole localization signal from Vigna mungo (1910332A) are shown. Bold-all amino acid residues identical at a given position; italicized most amino acids identical or conservative at given position; underlined-block of identical amino acids at given position;

FIG. 10 recombinant Ananain expressed in *Pichia pastoris*. Supernatant of expression culture of *Pichia pastoris* KM71H with Ananain activated (25 kDa arrow) from expressed Proenzyme (35 kDa arrow) in a yield of 12,5 mg/l (45 kDa arrow shows a secreted yeast protein); and FIG. 11 a scheme for amplification of cysteine proteases from the cDNA library: PCR with degenerated primers including all 9 primer variants with expected PCR products (in bp); amplification from 3' to 5' end by specific primers, which are complementary to an identical DNA section of the underlying alignment, with "nested" PCR and internal fragment; amplification of complete genes and amplification of sequence stb4 using cDNA as template cut by EcoRI.

According to a first embodiment of the present invention a heterologously expressed Bromelain protein or a fragment thereof is provided, wherein said Bromelain protein or fragment thereof has been heterologously produced in substantial amounts as soluble protein.

The term heterologously expressed used herein refers to protein expression in a host organism different from the organism of origin in general and in the present case to expression using as host a genus other than *Ananas*, i.e. not pineapple plant. Examples for such hosts comprise inter alia *Pichia pastoris*.

Bromelain protein as used herein refers to a single protease contained in any of the fractions of the Bromelain crude extract, which is distinguished from other proteases contained in Bromelain by its amino acid sequence. A fragment is a polypeptide of sufficient length to exhibit essentially the same function(s) as the protease itself. In order to ensure this, the fragment has enough length to cover the active site of the protease protein. In general, the activity of a protein is preliminary dependent of the active site and its closer surrounding affecting a particular three dimensional structure required for reactivity, whereas more distant stretches of amino acids, such as loops and sheets, influence the protein's substrate affinity and, on the proteins surface, access of the substrate and water solubility of the protein. Accordingly, a protein fragment of Bromelain encompassing the active site, may exhibit a protease activity towards different substrates and/or different substrate preferences. A fragment of a Bromelain protein may be either "naturally" derived, i.e. by permitting auto-digestion of the Bromelain protein, or artificially by e.g. cleavage of the Bromelain protein with any other Protease. It will be appreciated that the size of the fragment derived by auto-digestion may be easily adjusted by means of environmental parameters, such as concentration (in water as solvent), buffers, temperature and other parameters. The heterologously expressed Bromelain protein or fragment thereof as used herein comprises both the active Bromelain protein and the Bromelain proenzyme requiring activation by e.g. application of an acidic buffer system affording a shift to pH 4. The same issue applies to the fragments of the Bromelain proteins.

The term "substantial amounts" as used herein refers to active Bromelain protein or a fragment thereof heterologously expressed in an amount of >1 mg/l, preferably >2 mg/l, >4 mg/l, >6 mg/l, >8 mg/l or >10 mg/l, and more preferably in an amount of >12 mg/l.

The term "soluble" as used herein refers to a protein or fragment thereof exhibiting essentially the same three dimensional structures as the corresponding native, wild type protease. This ensures that the protein or fragment thereof exhibits the desired cysteine protease activity and that addition of other substances, for e.g. renaturation purposes may be avoided, which ensures on the one hand an improved tolerance upon ingestion and avoids on the other hand undesired modifications of the polypeptide. The folder protein or fragment thereof exhibits further to the surrounding enough hydrophilic amino acids, i.e. undergoing hydrogen bonds with water molecules, in that the protein or fragment thereof has a bioavailability rendering it suitable for use in medical purposes. The term bioavailability describes the rate and extent to which the active ingredient or active moiety is absorbed from a drug product and becomes available at the site of action. The bioavailability of orally ingested drugs is determined by factors, which include the nature of the molecule, its stability, and the formulation administered—and in the patient—such as a reduced intestinal surface area as a result of colic disease or intestinal resection and whether or not the drug is taken with a meal. Factors influencing the bioavailability may include, but are not limited to a poor absorption from the gastrointestinal tract, hepatic first-pass effect and a partial degradation of the drug prior to reaching system circulation. The present expression system permits unexpectedly high yields and an unexpected high solubility of the proteins or fragments thereof but also leads to higher amounts of active Bromelain proteins or fragments thereof as digestion by other proteases is avoided.

The present Bromelain proteins may be e.g. obtained by means of RNA isolation from plant material in a first step, e.g. by applying the TRIzol plus RNA Purification System (Invitrogen). DNA as well as proteins may be isolated by means of Trizol (Invitrogen). As starch destroys the gradient a further for separation of RNA from proteins is needed. Greater amounts of RNA from starch rich organs as stem may be isolated using the RNeasy Plant Mini Kit (Qiagen) thereafter. In a next step a cDNA library may be generated. This may be performed by any method known to the skilled person, e.g. by employing the SMART™ cDNA Library Construction Kit (Clontech). The cDNA may be ligated in a suitable plasmid or vector followed by transformation in e.g. *E. coli*. It will be appreciated that this may be performed by any method well known to the skilled person. The inserts may be sequenced by means of standard DNA sequencing techniques. For expression the DNA sequences may be ligated in a suitable expression vector under control of a constitutive or inducible promoter. A suitable expression system is e.g. pPICZalpha (Invitrogen), which may transformed by any suitable technique, such as electroporation, in a suitable host, such as *Saccharomyces cerevisiae, Candida albicans* or preferably *Pichia pastoris*. *Pichia pastoris* as host for heterologous expression exhibits the particular advantage that the glycosylation pattern corresponds essentially to those of higher eukaryotes, as homologues of the α-1,3-Mannosyl-transferase are not present in said organism.

Transformation and subsequent protein expression may be performed according to the protocols available in the state of the art. Activity of the expressed protein may be easily tested by employing casein as substrate, which is degraded to casein hydrolysate. This conversion may be e.g. quantitatively determined by means of spectrophotometer working at a wavelength in the visible range of e.g. 600 nm. Alternatively, casein may be included in the agar medium used for expression. Degradation of casein results in appearance of clear halos forming around the colonies. The required knowledge of recombinant DNA techniques may be derived from Maniatis et al.; Molecular Cloning: A Laboratory Manual 2nd ed., (1989).

It has been surprisingly found that by removing of the C-terminal propeptide, an element which function is not elucidated yet, the yields of the present Bromelain proteins were significantly enlarged by a factor 2, preferably factor 3, 4, 5 or 6, more preferably by a factor 10 or more in comparison to heterologous expression of a Bromelain protein still bearing the C-terminal propeptide. In particular, it could be shown that by removing of the C-terminal propeptide yields of 12.5 mg/l Ananain and in case of Papain from 1-2 mg/l were obtained.

Accordingly, in a first aspect of the present invention heterologously expressed Bromelain protein or a fragment thereof is provided, wherein DNA encoding the C-terminal propeptide of the corresponding Bromelain protein or a fragment thereof has been removed. Examples of DNAs encoding C-terminal propeptides are listed in FIG. 9. It will be appreciated that determination of the DNA sequences of C-terminal propeptides originating from other Bromelain proteins may be easily determined according to the knowledge of the skilled person.

The N-terminal propeptide acts in preventing autolysis of the cysteine protease. Accordingly, modification but also omission of N-terminal propeptide sequences are contemplated. It will be appreciated that the skilled person ma easily determine the respective sequences and alter them accordingly.

According to another aspect of the present invention heterologously expressed Bromelain protein or fragment thereof is provided. The protein or fragment thereof has a post-translational modification different from that conferred by the genus Ananasdepending on the expression system used.

By using an organism different from the genus *Ananas*, a distinct posttranslational modification (PTM) may be ensured referring in general to a chemical modification of a protein after its translation, wherein messenger RNA is decoded in order to generate a specific polypeptide or protein. PTMs may be classified according to their actions on the translated protein. They may confer addition of functional groups or other proteins/peptides, result in changing of chemical nature of the amino acids forming the protein and result in structural changes. An example of a posttranslational modification is the glycosylation during which saccharides are added to the protein. Particular a different glycosylation may result in a different water solubility, which may in turn positively affect bioavailability of the protein or peptide.

It will be also appreciated by those skilled in the art that the functions of Bromelain protein or fragments thereof may be achieved by a variety of different amino acid sequences, in that in another embodiment the heterologously expressed Bromelain protein or fragments thereof exhibit a sequence similarity to a Bromelain protein of at least 99%. Preferably, the sequence similarity is at least 99.5% and more preferably at least 99.8%. With other words, the sequences of protein or fragments thereof are distinguished from their respective wild-type counterparts by 1 amino acid per each 100 amino acids and preferably 2 amino acids per each 100 amino acids.

Such a protein or fragment thereof is a polypeptide containing changes in amino acid residues that are not essential for activity, i.e. differ in the amino acid sequence from the original Bromelain protein or fragment thereof, yet retain biological function or activity. For example, amino acids may be substituted at 'non-essential" amino acid residues. A "non-essential" amino acid residue is a residue that can be altered from the wild-type sequence a particular Bromelain protease without altering the biological function or the structural folds, whereas an "essential" amino acid residue is required for biological function. Similar functions are often complied by amino acids with similar structural or chemical properties, for example, replacement of leucine with isoleucine. More rarely, a variant may have "non-conservative" changes, for example, replacement of glycine with tryptophan. The same holds true not only for single amino acids residues, but for entire sequences of amino acids that may be added or omitted without altering the biological function of the protein. Hence, similar minor variations may also include amino acid deletions or insertions, or both. Very often, a short amino acid sequence within a much larger polypeptide is principally responsible for the biological activity or function of a protein.

Hence, the present invention also covers homologues of Bromelain proteins or fragments thereof. The homology or sequence similarity or sequence identity of protein sequences may easily be determined according to techniques well known in the art, e.g. by using established software or computer programs, e.g. the BLAST (Basic Local Alignment and Search Tool) program based on the work of Altschul, S. F. et al. (J. Mol. Biol.; 215 (1990) 403-410 and Nucleic Acids Res.; 25 (1997) 3389-3402) offering a set of similarity search programs designed to explore all of the available sequence databases regardless of whether the query is protein or DNA. The BLAST programs have been designed for speed, with a minimal sacrifice of sensitivity to distant sequence relationships. The scores assigned in a BLAST search have a well-defined statistical interpretation, making real matches easier to distinguish from random background hits. BLAST uses a heuristic algorithm which seeks local as opposed to global alignments and is therefore able to detect relationships among sequences which share only isolated regions of similarity. Said program is based on modified algorithms of Smith and Waterman (J. Mol. Biol.; 147 (1981) 195-197) and Sellers (Bull. Math. Biol.; 46 (1984) 501-514) to find the best segment of identity or similarity between two sequences. When using a sequence alignment program such as BLAST, to determine the degree of sequence homology, similarity or identity, the default setting may be used, or an appropriate scoring matrix, such as BLOSUM or PAM, may be selected to optimize identity, similarity or homology scores.

The present recombinantly produced Bromelain proteins may be used to elucidate the biological activity and role thereof in the plant.

In order to account for artificial modifications of the amino acid sequence that may be introduced for a variety of reasons, the present invention also encompasses sequences that are not homologues but that share at least a sequence similarity as defined above or the three-dimensional structure or the function of a Bromelain protein according to the present invention. It will be appreciated that particularly by exchange of single amino acids or by exchange of the glycosylation patterns different properties of the Bromelain protein or fragment thereof may be obtained. One effect of such an exchange may reside e.g. in an improved bioavailability, e.g. by obtaining a higher solubility in comparison to a protein or fragment thereof, which does not bear the particular exchange.

In still another embodiment of the present invention, the heterologously expressed Bromelain protein exhibits of any of SEQ ID. No. 1-4. The same applies for the present fragments covering a particular region of said proteins. SEQ ID. No. 1 and 2 represent hereby two stem Bromelain protein sequences; SEQ ID. No. 3 that from Ananain; and SEQ ID. No. 4 the amino acid sequence of fruit Bromelain (cf. FIG. 5*a-d*). Other preferred heterologously expressed Bromelain proteins are those listed in table 1. The yields of active protein exhibiting SEQ ID. No. 1-4 and those listed in table 1 are preferably enlarged by omission of the C-terminal propetide to the extent as indicated above. The DNA sequences corresponding to the proteins of SEQ ID. No. 1-4 are indicated by SEQ ID. No. 5-8 (cf. FIG. 6*a-d*).

It has been found that the Ananain DNA sequence with Seq. ID. No. 7 (corresponding to the protein with Seq. ID. No. 3, representing the protein with the highest content in Bromelain) differs from the sequences of the state of the art, which are incorrect.

According to another embodiment of the present invention a fragment of the heterologously expressed Bromelain protein comprises at least 50 amino acids, preferably at least 60, 70, 90, 100, 110, 120 and more preferably at least 130 amino acids. As set out above, the fragment will cover a region of the protein in which the active site of the Bromelain protein in question is localized. The activity of such fragments may be than assayed by means of techniques known to the skilled person, in order to select fragments bearing a protease activity.

Bromelain protein fragments may be generated by cloning and expressing respective nucleotide sequences. A nucleotide sequence encoding any of SEQ ID. No. 1-4, i.e. of SEQ ID. No. 5-8, or a nucleotide sequence encoding any of the proteins outlined in table 1 may be e.g. subjected to digestion with DNAse under suitable conditions to obtain nucleotide fragments of the desired lengths. The respective nucleotide fragments are than cloned in an expression plasmid in a suitable host, e.g. *Saccharomyces cerevisiae* or *Pichia pastoris*. The recombinant micro organism obtained may be plated on agar plates comprising growth medium for the yeast and the lipid triolein bestowing a milky appearance to the agar plates. Upon expression, which may be affected under control of a constitutive or inducible promoter, nucleotide fragments bearing the active site may be expressed in form of active Bromelain protein fragments. Since active fragments comprise the same activity as the full length Bromelain protein, digestion of triolein may occur resulting in appearance of clear halos around a colony. The nucleic acid sequence may be isolated from said colony for determining the DNA sequence and the respective peptide sequence. Other suitable assays comprise conversion of milky casein substrate to clear hydrolysis products or cleavage of peptides coupled with nitroanilide, wherein in case of presence of a suitable protease nitroanilide group is cleaved and may be detected spectrophotometrically at 405 nm. Such peptides coupled with nitroanilid comprise e.g. Arg-Arg-nitroanilide for Stem Bromelain or Phe-Val-Arg-nitroanilide for Ananain.

These and other suitable assays for the detection of activity of cysteine proteases or hydrolases in common may be found in Bornscheuer U. T., Kazlauskas, R. J., Hydrolases in Organic Synthesis, Wiley-VCH, Weinheim (Germany), 1999). The required knowledge of recombinant DNA techniques may be e.g. derived from Maniatis et al.; Molecular Cloning: A Laboratory Manual 2nd ed., (1989). It will be clear that in case the heterologous strains exhibits a high protease activity, a specific cysteine protease inhibitor, such as E64 (Merck), may be employed.

According to an embodiment of the present invention said posttranslational modification distinguishing the heterologously expressed protein or fragment thereof from the wild type protein results in a different glycosylation pattern. It is well known to the skilled person that different organisms used for heterologous expression of a polypeptide may confer a different glycosylation pattern affecting inter alia a bioavailability of the polypeptide.

According to still another embodiment the posttranslational modification of the heterologously expressed Bromelain protein or fragments thereof is conferred by a host organism selected under the group consisting of yeasts, insect cells and plant cells. The selection of such an expression host lies within the knowledge of the skilled person and comprises preliminary adapting of the codon usage of the nucleotide sequence encoding the Bromelain protein or fragment thereof in order to ensure a high expression. Codon usage refers to the phenomenon of preferences of different organisms for one of the several codons, i.e. triplet of nucleotides specifying an amino acid residue in a polypeptide, which encode the same given amino acid. In order to circumvent such preference it may be necessary to e.g. chemically synthesize the DNA encoding the Bromelain chain or fragment thereof, in which the codon usage is adapted to the chosen expression host. This is within the knowledge of the skilled person. Expression of the heterologous protein of fragment thereof may be e.g. performed according to Bromme D et al. (Methods 32 (2004) 199-206). It will be appreciated that conditions for expression, comprising inter alia temperature, medium, kind of vessel, aeration, etc., are within the knowledge of the skilled person.

As a particular suitable expression host, *Pichia pastoris* has been approved. Said strains produce low amounts of proteases, which have found not to disturb expression of Bromelain proteins and fragments thereof as well as respective assays on protease activity. Preferred *P. pastoris* strains are KM71 or KM71H. which permit integration in the AOX2-Locus and slew methanol metabolisation. It is assumed that by the slow methanol consumption and corresponding slow production rate of protein or fragments, correct folding and secretion thereof is rendered possible. Expression in *Pichia pastoris* using a suitable plasmid, such as pPIC9 or pPICZalpha (both from Invitrogen), ensured high transcription and translation rates. In addition, the Bromelain protein or fragment thereof maintained solubility and further degradation of the active peptide was reduced or even avoided. The present Bromelain protein or fragment thereof exhibited further no significant toxicity to the host organism. Another advantage of using a yeast, such as *Pichia pastoris*, as expression host resides in the possibility to perform downscaling of growth experiments, i.e. by using microtiter plates with e.g. 96 wells instead of flasks. This ensures high throughput for testing on properties, such as the ability to degrade casein. The ability to degrade casein by exerting a cysteine protease activity is in turn indicative for an underlying medical activity, which corresponds at least in part to that of Bromelain.

According to still another embodiment of the present invention, the heterologously expressed Bromelain protein or fragments thereof carry means permitting purification of the Bromelain protein or fragments thereof. Such techniques are well known to the skilled person and may be for example performed by generating and expressing a fusion peptide of the Bromelain protein or fragment thereof with a particular amino acid sequence, which may reversibly bind to the matrix of a column material. The amino acid sequence may be for example a poly-histidine tag sequence fused to the N- or C-terminus of the peptide to be purified. After protein expression the tag binds to the affinity material and released by means of an imidazole gradient, thereby separating the fusion protein or fusion peptide from other proteins and fragments. If required, the tag may be removed. Such techniques are well known to the skilled person. It will be appreciated that any kind of tag may be used in the present invention.

It has been found by the present inventors that of particular advantage is fusion of the tag at the N-terminal site of the Bromelain protein or fragment thereof since in said case not only the propetide but also the tag sequence is removed after acidification. This offers the possibility to avoid removal of the tag by any other means, such as an endoprotease.

According to a preferred embodiment the inclusion of heterologously expressed Bromelain protein or fragments thereof in a pharmaceutical, dermatological or nutritional composition is envisaged.

According to another embodiment, the compositions of the present invention are formulated in any suitable manner for ingestion. The nutritional composition may be prepared directly before ingestion or alternatively during the manufacturing process. The nutritional compo-sition in the directly usable form is, however, preferred. The active ingredient is contained in acceptable excipients and/or carriers for oral consumption. The expression "nutrionally or pharmaceutical acceptable carrier" refers to a vehicle, for either nutritional or pharmaceutical use, which delivers the active component to its site of action and will not cause significant harm to the human or animal recipient. The actual form of the carrier is, however, not critical.

The total amount of the carrier preferably ranges from about 10 to about 99.9%, more preferably from about 50 to about 90% and still more preferably from about 70 to about 85% by weight of the formulation.

The pharmaceutically acceptable carrier or medicament may be in form of a liquid, gel, gelcap, capsule, powder, solid tablet (coated or non-coated), dried oral supplement, wet oral supplement, dry tube-feeding or wet tube-feeding or the like. The carrier is preferably in the form of a tablet or capsule and most preferably in the form of a hard gelatin capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof).

Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 8.0, preferably at a pH of about 6.0 to 7.0. A suitable enteric coating that dissolves in the small intestine but not in the stomach is cellulose acetate phthalate. Further details on techniques for formulation for and administration may be found in the latest edition of Remington's Pharmaceutical Sciences (Maack Publishing Co., Easton, Pa.).

Other suitable pharmaceutically acceptable carriers for use with the present invention include, but are not limited to, water, mineral oil, ethylene glycol, propylene glycol, lanolin, glyceryl stearate, sorbitan stearate, isopropyl myristate, isopropyl palmitat, acetone, glycerol, phosphatidylcholine, sodium cholate, or ethanol.

The composition according to the invention can also comprise at least one co-emulsifier, which includes, but is not restricted to, oxyethylenated sorbitan monostearate, fatty alcohols such as stearyl alcohol or cetyl alcohol, or esters of fatty acids and polyols such as glyceryl stearate.

Preferably, the pharmaceutical compositions of the present invention are stabilized. In general, stabilization methodologies and techniques that may be used in accordance with the present invention include any and all methods for the stabilization of chemical or biological material known to the art, including e.g. the addition of chemical agents, temperature modulation based methodologies; radiation based methodologies or combinations thereof. Chemical agents that may be used in accordance with the present invention include inter alia preservative agents; acids; bases; salts; anti-oxidants; viscosity modifying agents; emulsifiers; gelling agents; and mixtures thereof.

A wide variety of emulsifiers can be used to provide a beneficial effect in the present compositions, and the particular levels of use in connection with each type or class of emulsifiers can be readily determined. In general, a selected emulsifier or emulsifier system should be capable of maintaining different components of the nutritional composition in a stable dispersion, when the base is dispersed in an aqueous medium. In most cases when the base is dispersed in water, the emulsifier should be capable of forming stable oil-in-water emulsions. In particular, the emulsifier is preferably selected from the group consisting of: stearyl-n-lactylic acids, where n ranges from about 1 to 5, and the sodium, potassium and calcium salts thereof, succinylated mono- and diglycerides of edible C12-C24 fatty acids and the sodium and potassium salts thereof, diacetyl tartaric acid esters of mono- and diglycerides of C12-C24 edible fatty acids, and the sodium and potassium salts thereof, polyglycerol esters of C12-C24 edible fatty acids, ranging from 3 to 10 glycerol units and one to ten fatty acids per molecule, polyoxyethylene (20) sorbitan mono-, di- and triesters of C12-C24 edible fatty acids, ethoxylated mono- and diglycerides of edible C12-C24 fatty acids, stearyl monoglyceridyl citrate, and the sodium and potassium salts thereof, citric acid esters of mono- and diglycerides of edible C12-C24 fatty acids, and the sodium and potassium salts thereof, propylene glycol mono- and diesters of edible C12-C24 fatty acids, glycerol mono- and diesters of edible C12-C24 fatty acids, lactylated propylene glycol and glycerol mono- and diesters of edible C12-C24 fatty acids, acetylated propylene glycol and glycerol mono- and diesters of edible C12-C24 fatty acids, sorbitan monostearate, lecithin, sucrose esters of edible C12-C24 fatty acids, phosphated mono- and diglycerides of edible C12-C24 fatty acids, and mixtures thereof. Most preferably, the emulsifier is anionic and is selected from the group consisting of sodium stearyl-2-lactylate, succinylated mono- and diglycerides of edible C12-C24 fatty acids, diacetyl tartaric acid esters of mono- and diglycerides of C12-C24 fatty acid esters in their acid or salt form, and mixtures thereof.

In other embodiments, the supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food.

The present invention provides nutritional compositions or supplements (e.g. energy bars or meal replacement bars or beverages) comprising 5-D-fructose dehydrogenase as active ingredient. The nutritional supplement may serve as meal or snack replacement and generally provide nutrient calories. Preferably, the nutritional supplements provide carbohydrates, proteins, and fats in balanced amounts. The nutritional supplement can further comprise carbohydrate, simple, medium chain length, or suitable polysaccharides, or a combination thereof.

Sugars may be added. It should be clear that sugars forming fructose either by degradation or chemical/enzymatic conversion have only a limited application and may be incorporated only in case of a particular indication. However, a simple sugar may be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono- or disaccharides. The nutritional supplement may contain combinations of sources of carbohydrate of three levels of chain length (simple, medium and complex; e.g., sucrose, maltodextrins, and uncooked cornstarch).

Sources of protein to be incorporated into the nutritional supplement of the invention can be any suitable protein utilized in nutritional formulations and can include whey protein, whey protein concentrate, whey powder, egg, soy flour, soy milk soy protein, soy protein isolate, caseinate (e.g., sodium caseinate, sodium calcium caseinate, calcium caseinate, potassium caseinate), animal and vegetable protein and mixtures thereof. When choosing a protein source, the biological value of the protein should be considered first, with the highest biological values being found in caseinate, whey, lactalbumin, egg albumin and whole egg proteins. In a preferred embodiment, the protein is a combination of whey protein concentrate and calcium caseinate. These proteins have high biological value; that is, they have a high proportion of the essential amino acids. See Modern Nutrition in Health and Disease, eighth edition, Lea & Febiger, publishers, 1986, especially Volume 1, pages 30-32. Examples of the whey proteins include whey powder obtained by concentrating and drying whey, whey protein concentrate (WPC) obtained by concentrating whey by ultrafiltration (UF) and then drying, defatted WPC (low fat and high protein content) obtained by removing fat from whey, followed by UF concentration, WPI obtained by selectively isolating only protein from whey, desalted whey obtained by nanofiltration concentration, and mineral concentrated whey in which mineral components derived from whey have been concentrated.

The nutritional supplement can also contain other ingredients, such as one or a combination of other vitamins, minerals, antioxidants, fiber and other dietary supplements (e.g., protein, amino acids, choline, lecithin, omega-3 fatty acids). Selection of one or several of these ingredients is a matter of formulation, design, consumer preference and end-user. The amounts of these ingredients added to the dietary supplements of this invention are readily known to the skilled person. Further vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamine mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide.

Flavors, coloring agents, spices, nuts and the like can be incorporated into the product. Flavorings can be in the form of flavored extracts, volatile oils, chocolate flavorings, peanut butter flavoring, cookie crumbs, crisp rice, vanilla or any commercially available flavoring. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee. In one embodiment, the dietary supplement contains cocoa or chocolate.

Emulsifiers may be added for stability of the final product. Examples of suitable emulsifiers include, but are not limited to, lecithin (e.g., from egg or soy), and/or mono- and diglycerides. Other emulsifiers are readily apparent to the skilled artisan and selection of suitable emulsifier(s) will depend, in part, upon the formulation and final product. Preservatives may also be added to the nutritional supplement to extend product shelf life. Preferably, preservatives such as potassium sorbate, sodium sorbate, potassium benzoate, sodium benzoate or calcium disodium EDTA are used.

The nutritional supplement may contain, depending on the knowledge of the skilled person and the respective application, natural or artificial (preferably low calorie) sweeteners, e.g. particular saccharides, cyclamates, aspartamine, aspartame, acesulfame K, and/or sorbitol which are considered as be. Such artificial sweeteners can be desirable if the nutritional supplement is intended to be consumed by an overweight or obese individual, or an individual with type II diabetes who is prone to hyperglycemia.

The nutritional composition may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like. For example, the nutritional composition of the present invention may contain one or more of the following: asorbates (ascorbic acid, mineral ascorbate salts, rose hips, acerola, and the like), dehydroepiandosterone (DHEA), Fo-Ti or Ho Shu Wu (herb common to traditional Asian treatments), Cat's Claw (ancient herbal ingredient), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), spirulina, zinc, and the like. Such optional ingredients may be either naturally occurring or concentrated forms.

The nutritional supplement can be provided in a variety of forms, and by a variety of production methods. In a preferred embodiment, to manufacture a food bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled. The bars may contain other nutrients and fillers to enhance taste, in addition to the ingredients specifically mentioned herein. The present invention provides further food products, prepared food products, or foodstuffs comprising 5-D-fructose dehydrogenase. For example, in some embodiments, beverages and solid or semi-solid foods comprising 5-D-fructose dehydrogenase are provided. These forms can include, but are not limited to, beverages (e.g., soft drinks, milk and other dairy drinks, and diet drinks), baked goods, puddings, dairy products, confections, snack foods, or frozen confections or novelties (e.g., ice cream, milk shakes), prepared frozen meals, candy, snack products (e.g., chips), soups, spreads, sauces, salad dressings, prepared meat products, cheese, yogurt, chocolate, milk, yoghurt, curd, cheese, fermented milks, milk based fermented products, ice-creams, fermented cereal based products, milk based powders, infant formulae or pet food and any other fat or oil containing foods, and food ingredients (e.g., wheat flour).

In many forms of the present invention, it is necessary or desirable to add optional ingredients for imparting desired organoleptic or nutritional properties to the product. Such agents are well known to those skilled in the art and may include those selected from the group consisting of vitamins, minerals, flavoring agents, sweeteners (e.g., sucrose or other sugars), coloring agents, salt, pH adjustment agents, buffers, stabilizers, essential amino acids, anti-caking agents, antifoaming agents, and mixtures thereof. Again, these optional ingredients can be used in minor amounts as needed for creating desirable properties in the end products.

The nutritional composition of the present invention may further contain a food fiber. The food fiber may either be water soluble food fiber or non-water-soluble food fiber. Examples of the water soluble food fiber include sparingly digestible dextrin, pectin, glucomannan, alginic acid, hydrolyzate of alginic acid, guar gum, product of guar gum obtained by enzymolysis, and galactomannan. Sparingly digestible dextrin is preferred because it can be easily added to food and does not disturb food processing. Examples of the non-water-soluble food fiber include crystalline cellulose, soybean food fiber, wheat bran, corn fiber and beat fiber.

Other compounds suitable for use in combination with 5-D-fructose dehydrogenase in the preparation of a respective carrier include one Or more of vitamin actives, including but not restricted to vitamin A and derivatives, including retinoic acid, retinyl aldehyde, retin A, retinyl palmitat, adapalene, and beta-carotene; vitamin B (panthenol, provitamin B5, panthenic acid, vitamin B complex factor); vitamin C (ascorbic acid and salts thereof) and derivatives such as ascorbyl palmitat; vitamin D including calcipotriene (a vitamin D3 analog) vitamin E including its individual constituents alpha-, beta-, gamma-, delta-tocopherol and cotrienols and mixtures thereof and vitamin E derivatives including vitamin E palmitat, vitamin E linolate and vitamin E acetate; vitamin K and derivatives; vitamin Q (ubiquinone) and mixtures thereof. Preferably, the compositions of the present invention are stabilized. In general, stabilization methodologies and techniques that may be used in accordance with the present invention include any and all methods for the stabilization of chemical or biological material known to the art, including e.g. the addition of chemical agents, temperature modulation based methodologies; radiation based methodologies or combinations thereof. Chemical agents that may be used in accordance with the present invention include inter alia preservative agents; acids; bases; salts; anti-oxidants; viscosity modifying agents; emulsifiers; gelling agents; and mixtures thereof.

Compositions of the invention may also include viscosity modifiers, preferably in amounts from about 0.01 to about 10% by weight of the composition. Viscosity modifiers such as cetyl alcohol, glycerol, polyethylene glycol (PEG), PEG-stearate, or Keltrol may also be used to enhance the stability of the formulation. Thickeners which may enhance the stability include gelling agents such as cellulose and derivatives, Carbopol and derivatives, carob, carregeenans and derivatives, xanthane gum, sclerane gum, long chain alkanolamides, bentone and derivatives, Kaolin USP, Veegum Ultra, Green Clay, Bentonite NFBC, magnesium aluminum silicate (Veegum@), guar gums (such as JaguarHP-120 @), xanthan gum, sodium caroxymethyl cellulose, hydroxyalkyl and alkyl celluloses, cross-linked acrylic acid polymers, and mixtures thereof. As known to the skilled person, the precise amount of thickeners can vary depending upon the consistency and thickness of the composition which is desired.

The nutritional and pharmaceutical compositions are administered in an amount to be effective for the intended application and the subject to be treated. To this end, the dosage of the composition and other constituents may vary depending on age, weight, and condition of the subject. In general, the active agent is preferably administered at a concentration that will afford effective results without causing any harmful or deleterious side effects, and may be administered either as a single unit dose, or if desired in convenient subunits administered at suitable times throughout the day.

The nutritional or pharmaceutical composition of the present invention may be administered multiple times a day, for example, from two to five times adding up for the necessary amount for one day, once a day, or continuously for a necessary term.

A pharmaceutical composition may be prepared e.g. by a wet granulation process, in which the active compounds in powder form are presented in a suitable granulator and subsequently moistened or sprayed with molten material. The shear forces applied lead to an intensive mixing of the powder and, with the addition of binder solutions, to the rapid formation of high-density granulates. Granulation is required to improve the flow of powder mixtures and mechanical properties of tablets. Granules are usually obtained by adding liquids (binder or solvent solutions). Larger quantities of granulating liquid produce a narrower particle size range and coarser and harder granules, i.e. the proportion of fine granulate particles decreases. The optimal quantity of liquid needed to get a given particle size should be known in order to keep a batch-to-batch variations to a minimum. Wet granulation improves flow, compressibility, bioavailability, homogeneity, electrostatic properties, and stability of solid dosage forms.

According to another embodiment, the present pharmaceutical composition is a solid dosage form. Exemplary solid dosage forms of the invention include tablets, capsules, sachets, lozenges, powders, pills or granules. The solid dosage form may be, for example, immediate release dosage form, a fast melt dosage form, controlled release dosage form, lyophilized dosage form, delayed release dosage form, extended release dosage form, pulsatile release dosage form, mixed immediate release and controlled release dosage form, or a combination thereof. A solid dose tablet formulation is preferred. The solid dosage form is preferably an immediate release dosage form offering advantages regarding the bioavailability of the active compounds.

If an immediate release dosage form is chosen, it will be clear for the skilled person that the amount of release controlling agent(s) to be used in forming the outer portion will be determined based on various parameters such as the desired delivery properties, including the amount of active ingredient or substance to be delivered, the a active ingredient or substance release rate desired, and the size of the micro matrix particles.

The immediate release dosage form may also include a material that improves the processing of the release controlling agents. Such materials are generally referred to as plasticisers. Preferred plasticizers include acetylated monoglycerides, butyl phthalyl butyl glycolate, dibutyl tartrate, diethyl phthalate, dimethyl phthalate, ethyl phthalyl ethyl glycolate, glycerin, ethylene glycol, propylene glycol, triethyl citrate, triacetin, tripropinoin, diacetin, dibutyl phthalate, acetyl monoglyceride, polyethylene glycols, castor oil, triethyl citrate, polyhydric alcohols, acetate esters, glycerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylhexyl phthalate, di-n-octyl phthalate, dioctyl phthalate, di-i-decyl phthalate, di-n-undecyl phthalate, di-n-tridecyl phthalate, tri-2-ethylexyl trimellitate, di-2-ethylexyl adipate, di-2-ethylhexyl sebacate, di-2-ethylhexyl azelate, dibutyl sebacate, glyceryl monocaprylate, glycerol distearate and glyceryl monocaprate.

The dosage form may be manufactured according to the following procedure: The core particles may be produced in accordance with usual techniques in which the active ingredient or substance and one or more release controlling agents are mixed and granulated by adding solvent in a low or high shear mixer or by fluidized bed granulator. The granulate is dried, for example in a fluidized bed dryer. The dried granulate is sized. The sizing of the micromatrix particles may be performed by using an oscillating granulator, comminuting mill or any other conventional method. The sieve used for the sizing may have openings from 0.25 mm to 5 mm. Alternatively, the core particles can be made by extrusion, spheronization, melt granulation or by roller compaction. The core particles may be coated by a solution of one or more release controlling agents by any known method, including spray application. Spraying can be carried out using a fluidized bed coater (preferably Wurster coating), or in a pan coating system. Alternatively the coating of the core particles with one or more rate controlling agents can be done by hot melt process using a granulator or fluidized bed coater (preferably Wurster coating), or in a pan coating system. The compression of micro tablets is carried out on usual compression machines (e.g. machines by Manesty, Cadmach or Kilian). The micro tablets can be made of various sizes and shapes like round, oval, oblong, capsule shaped, triangular, square, etc. The preferred shape of the micro tablet is round, biconvex and the preferred diameter of the micro tablet is 1.5 mm to 9.5 mm.

The micro tablets may be coated by a solution of one or more release controlling agents by any known method, including spray application. Spraying can be carried out using a fluidized bed coated (preferably Wurster coating), or in a pan coating system.

Alternatively the coating of the micro tablets with one or more rate controlling agents can be done by hot melt process using a fluidized bed coated (preferably Wurster coating), or in a pan coating system. The micro tablets can be filled in the casing using manually operated, semiautomatic or automatic capsule filling machine.

The present composition may by also present in a particular dosage form for improving the bioavailability of the present proteins or fragments thereof. The term bioavailability describes the rate and extent to which the active ingredient or active moiety is absorbed from a drug product and becomes available at the site of action. The bioavailability of orally ingested drugs is determined by factors, which include the nature of the molecule, its stability, and the formulation administered—and in the patient—such as a reduced intestinal surface area as a result of colic disease or intestinal resection and whether or not the drug is taken with a meal. Factors influencing the bioavailability may include, but are not limited to a poor absorption from the gastrointestinal tract, hepatic first-pass effect and degradation of the drug prior to reaching system circulation.

Different particle size fractions of the present protein or fragment thereof can be used. The preferred particle size of $d_{90}$ is less than 100 µm, more preferably less than 50 µm, most preferably less than 10 µm.

According to another embodiment, the present pharmaceutical composition may contain in addition to the Bromelain protein or fragments thereof one or more diluents, binding agents, disintegrants, lubricants, sweeteners, glidants, flavourings, colouring agents and other excipients, depending on the dosage form desired.

Suitable diluents include pharmaceutically acceptable fillers such as lactose, microcrystalline cellulose, dibasic calcium phosphate, saccharides and/or mixtures of the foregoing. Examples of diluents include microcrystalline cellulose, such as Avicel PH 101® and Avicel® PH 102; lactose such as lactose monohydrate, lactose anhydrous and Pharmatose® DCL 21; dibasic calcium phosphate such as Emcompress®; mannitol, starch, sorbitol, sucrose and glucose. The most preferred are microcrystalline cellulose and lactose.

Binding agents are preferably selected from polyvinylpyrolidone, starch grades (pregellatinized or plain), cellulose derivatives such as hydroxypropylmethylcellulose (HPMC), hydroxypropylcellulose (HPC) and carboxymethylcellulose (CMC) and their salts and gelatine, the most preferred is HPMC.

Suitable disintegrants include croscarmellose sodium, crospovidone, sodium starch glycolate, corn starch, potato starch, maize starch and modified starches calcium silicates, low substituted hydroxypropylcellulose and the like. Most preferred is croscarmellose sodium.

Lubricants are preferably selected from the group consisted of magnesium stearate, magnesium lauryl sulfate and sodium stearyl fumarate, sucrose esters or fatty acid, polyethylene glycol, stearic acid and the like.

Sweeteners are preferably selected from the group consisting of aspartame, saccharin sodium, dipotassium glycyrrhizinate, aspartame, stevia, thaumatin, and the like.

Glidants are preferably selected from the group consisting of silicon dioxide, talc and aluminium silicate.

As flavourings, colouring agents, or opacifying agents and pigments any suitable compound known to the skilled person may be used.

The present inventors have found that the positive effects assigned to Bromelain may be also accorded to the particular proteins and fragments thereof. Due to the inherent advantages of recombinant techniques, the present proteins and fragments may be obtained with higher purity, particularly avoiding the presence of other proteins or protein fragments, leading to decreased side effects. It has also found that the present Bromelain proteins or fragments thereof have, even in aqueous solution, higher storage stability over a long period. The positive effects from Bromelain proteins or fragments thereof comprise edeme reducing, hemolytic, fibrinolytic, anti-inflammatory, anti-metastatic and tumor inhibitory properties. Additionally, stimulating effects on the immune system, such as acceleration of wound healing may be expected.

Accordingly, another preferred embodiment of the present in pertains to the use of a Bromelain protein or a fragment thereof for the preparation of a medicament for the prevention and/or treatment of cancer, atherosclerosis, bacterial infections, inflammations, thromboses and edema. Particularly, Ananain may be used for the prevention and/or treatment of cancer as well as inhibiting the formation of metastasis as Ananain is found in fraction F9, isolated according Harrach and Maurer (1996), which has already proven to be effective in inhibition of activation of ERK-2.

The present invention is illustrated by the following examples without limiting it thereto.

EXAMPLES

Unless stated otherwise, recombinant DNA techniques have been performed according to Maniatis et al.; Molecular Cloning: A Laboratory Manual 2nd ed., (1989). Purified water was obtained by employing a PURELAB ultra (ELGA).

RNA Isolation

RNA but also DNA and proteins were isolated using the Qiazol kit (Invitrogen) following the manufacture's instructions: Mix 1 ml Qiazol with plant material for 50-100 mg fresh weight. To remove polysaccharides, the mixture was centrifuged 10 min, 12.000×g, at room temperature. Supernatant was incubated 5 min at 30° C. Chloroform was added in an amount of 0.2 ml per ml Qiazol. The solution was mixed thoroughly for 15 sec. The mixture was incubated at 30° C. for min. Then the mixture was centrifuged for 15 min., at 4° C., 2.000×g. The upper phase, containing RNA, was removed and mixed with 0.5 ml isopropanol per ml Qiazol. The mixture was centrifuged 10 min, at 4° C., 12.000×g and the supernatant removed. The RNA pellet was washed with 1 ml 75% Ethanol (made with DEPC-water) per ml Qiazol, mixed thoroughly and centrifuged 7500×g, 5 min, 4° C. After removal of the supernatant, the pellet was resuspended in RNase free water.

Greater amounts of RNA free from DNA and proteins from pineapple stem were obtained using the RNeasy Plant Mini Kit (Qiagen) additionally thereafter.

Preparation of a Genomic cDNA Library

For preparation of the genomic cDNA library the SMART IV™ cDNA Library Construction Kit (Clontech) was used. First and second strand synthesis, digestion with proteinase K, digestion with SfiI, cDNA size exclusion fractionation, ligation of the SfiI cut cDNA in SfiI cut, dephosphorylated pDNR-LIB vector and transformation of the obtained insert containing vector was performed according to the manufacture's instructions.

Preparation of PCR Products with Degenerated Primers

The sequences of degenerated primers were generated using the program "Codehop" available on the internet at: bioinformatics.weizmann.ac.il/blocks/codehop.html) and the codon usage from *Oryza sativa* as rice having a similar GC content as *A. comosus* and belonging to the same order of Poales. Underlying sequences were those of stem bromelain stb1 (Acnr[1]: P 14518), Ananain an1 (Acnr[1]: CAA05487), fruit Bromelain fb1 (Acnr[1]: D14059) stb2 (Acnr[1]: AC09829) and stb3 (Acnr[1]: AC09830). Table 2 shows the primers employed for PCR (concentration 100 pmol/µl).

The PCR reaction for colony PCR comprised a single step of 94° C. for 5 min. and 30 cycles of each 94° C. for 1 min+54° C. for 1 min+72° C. for 1 min, followed by 72° C. for 7 min. and storage at 4° C.

PCR reactions for amplification of sequences for cloning purposes comprised a single step of 98° C. for 1 min. and 25 cycles of each 98° C. for 8 sec.+59° C. for 20 sec.+72° C. for 25 sec., followed by 72° C. for 5 min. and storage at 4° C.

The PCR reaction was performed according to manufacturer's instructions in HF buffer for high fidelity with Phusion™ Polymerase.

Phusion-Polymerase; NEB

---

10 µl 10x buffer HF (NEB)
0.5 µl primer A (100 pmol/µl)
0.5 µl primer B (100 pmol/µl)
0.5 µl dNTP-Mix (10 mM, Fermentas)
x µl ddH$_2$0
0.2 µl Phusion (2.0 U/µl) (NEB)
x ng DNA 50 µl Σ sterile water

---

As template pDNR-LIB containing cDNA fragments was used. Amplified sequenced were subcloned pCRII by TOPO TA Cloning® Kit (Invitrogen), as instructed by manufacturer.

Colony PCR was performed using taq-Polymerase (Fermentas). Therefore all components were pipetted and cell material was added to the reaction.

Colony PCR:

---

5 µl 10X buffer
5 µl 25 mM MgCl$_2$
1 µl 25 mM dNTPs

-continued

| | |
|---|---|
| 1 µl | 5' AOX1 primer (10 pmol/µl) |
| 1 µl | 3' AOX1 primer (10 pmol/µl) |
| 27 µl | sterile water |
| 5 µl | cell material |
| 45 µl | total volume |

The PCR reactions, which were all conducted with sterile PCR reaction vessels (Eppendorf, Hamburg, Germany) in a Mastercycler Gradient (Eppendorf, Germany), were separated by means of a conventional SDS agarose gel, excised and purified by means of the NucleoSpin® Plasmid-DNA Kit (Macherey & Nagel, Düren, Germany) or Microspin Columns (Amersham Pharmacia) for sequencing. The products were cloned in pTOPO-PCRII (Invitrogen). Gels were performed by means of a Mighty Small SE250/SE260 (Hoefer) employing SUB-CELL® GT or MINI-SUB-CELL® GT (both Biorad). As centrifuges the Avanti J E cooling centrifuge (Beckmann Coulter), Biofuge pico or Biofuge fresco (both Heraeus) were used.

Sequencing

As bromelain proteins exhibit in general a high sequence similarity of 95% or more among each other, sequences fulfilling this criterion with respect to already known Bromelain proteins (cf. FIG. 1) have been used for further evaluation. DNA Sequencing has been performed according to manufacture's instruction with a capillary sequencer (MWG).

Cloning/Growth Conditions

The sequences of two stem Bromelains (FIGS. 6a and 6b), Ananain (FIG. 6b) and fruit Bromelain (FIG. 6c) have been cloned in frame in pPIC9 or pPICZA (both Invitrogen) using EcoRI and NotI restriction sites, which is shown for stb3 (Acnr[1]: AC09830) in FIG. 7. Cloning has been performed with a Gene pulser/Pulse Controller (both Biorad) according to the manufacture's instructions.

In this respect it has been found that protein expression carried out according to the EasySelect™ PichiaExpression Kit did not yield any clones in that several modifications have been applied. The vector has been linearised with BglII instead of SacI prior application of EcoRI and NotI as BglII linearisation permits a high salt buffer more suitable in case of high amounts of DNA. It has been further found that the cells may be grown in standard 96 well microtiter plates using 250 µl of growth medium and antibiotic for selection, permitting high density screening for active clones. Induction was performed at OD600 of approximately 4 (4±0.2), which is obtained for all wells after 60 h. To this point glycerine was completely consumed, in that all wells exhibited essentially the same optical density of 4. For the first induction 250 µl of minimal medium with 2× methanol concentration has been employed, whereas subsequent inductions were carried out all 12 h with 50 µl minimal medium with 10× methanol concentration.

As control pPICZ/gfp was used, which was kindly obtained by Glieder, T U Graz). Said plasmid comprises gfp (Shimomura O. et al., J. Cell. Comp. Physiol., 59 (1962), 223-239; Shimomura O., J. Microsc., 217 (2005), 1-15), employing the same restriction sites and the same conditions for growth and induction.

100 µl supernatant of *Pichia pastoris* expression cultures Ant (Acnr[1]: CAA05487), which is obtained in the same way as STB3, and has been subjected to SDS-Page using standard conditions (cf. FIG. 2).

Assay on Protease Activity

100 µl supernatant of *Pichia pastoris* expression cultures in BMM minimal medium or BMMY complete medium were diluted with buffer (pH 4) for cleaving off the proenzyme. The solution was subsequently incubated for 30 min. at 55° C. and casein was added resulting in a final concentration of 1%. OD600 was determined after 1 hour incubation at room temperature using a standard microtiter plate reader (cf. FIG. 4).

*P. pastoris* comprising pPICZA with alpha factor, propeptide and Ananain (Anl) but without C-terminal cysteine protease sequence, exhibited the best results. 12 mg/l active AN1 was obtained (casein as substrate) in 1 l of BMM medium (pH 6) grown for up to 48 h in shaking flasks equipped with three or four baffles at 230 rpm and 28° C., employing a Unitron HT shaking incubator (Infors). The Proananain exhibited after 7 days storage at 4° C. 90% of the initial activity towards casein as substrate.

Maldi-Tof Analysis of Bromelain Proteins

Samples from the supernatants were taken after 3d of cultivation and purified with Zip-Tips (Millipore) before subjecting to Maldi-T of Analysis employing a 4800 TOF/TOF mass analyser (Applied Biosystems).

It could be derived that the secretion signal was cleaved off in a correct manner. The proteins expressed in *P. pastoris* exhibited glycosylation as verified with the Glykomod tool (available on the world wide web at: ExPASy.ch; results not shown).

TABLE 1

| Designation | Accession No. | Reference | Gene | Protein |
|---|---|---|---|---|
| Ananain | S46204 | Napper, A. D. et al.; Biochem. J.; 301 (1994) 727-735 | — | AN1 |
| PreproAnanain | AC09829 | Lee, K. L. et al.; Biochem. J.; 327 (1997) 199-202 | an2 | AN2 |
| Stem Bromelain | S03964 | Ritonja, A. et al.; FEBS Lett.; 247 (1989) 419-424 | — | STB1 |
| Prepro stem Bromelain | CAA08860 | Robertson, C. E. a. G. P. W.; Report (1998) | stb3 | STB2 |
| Prepro stem Bromelain | D38532 | Muta, E. et al.; Report (1994) | stb2 | STB3 |
| Prepro stem Bromelain | — | — | stb4 | STB4 |
| Fruit Bromelain | D14057 | Muta, E.; Report (1993) | fb1 | FB1 |
| Fruit Bromelain CCX | — | Mynott T. L.; WO 00/14253 | fb | FB2 |

TABLE 2

| SEQ ID No. | Name | Sequence | Description |
|---|---|---|---|
| 9 | Cysprot_c_down | CCGTAGCCGATGATGGTGAYNGCRTGRTT | Amplification of cysteine proteases from cDNA-library of A. comosus |
| 10 | Cysprot_d_down | CCNGGNACRCCGTGGAGGGACTTGGT | Ampl. of cysteine proteases from cDNA |
| 11 | Cysprot_1_up | CCNGGNACRCCGTGGAGGGACTTGGT | Ampl. of cysteine proteases from cDNA |
| 12 | Cysprot_3_up | GCCACCGTGGAGTCCATCTAYAARATHAA | Ampl. of cysteine proteases from cDNA |
| 13 | Cysprot_a_down | CAGCGGGTCCATGGCDATNCCRCA | Ampl. of cysteine proteases from cDNA |
| 14 | Cysprot_b_down | GAACACGCCGCGCTTRTARTRYTG | Ampl. of cysteine proteases from cDNA |

REFERENCES

1. Cregg, J. M., J. L. Cereghino, J. Shi, and D. R. Higgins. 2000. Recombinant protein expression in *Pichia pastoris*. Mol. Biotechnol. 16:23-52.
2. Cregg, J. M., T. S. Vedvick, and W. C. Raschke. 1993. Recent advances in the expression of foreign genes in *Pichia pastoris*. Biotechnology (N.Y.) 11:905-910.
3. Thompson, J. D., D. G. Higgins, and T. J. Gibson. 1994. CLUSTAL W: improving the sensitivity of progressive multiple sequence alignment through sequence weighting, position-specific gap penalties and weight matrix choice. Nucleic Acids Res. 22:4673-4680.

What is claimed is:

1. A heterologously expressed, soluble, fragment of Bromelain protein having cysteine protease activity wherein the fragment comprises
   (a) at least 130 consecutive amino acids of the amino acid sequence of SEQ ID NO:1, and
   (b) the active site of the Bromelain protein, wherein the C-terminal propeptide from position 326 to position 359 of SEQ ID NO:1 is not present in said fragment.

2. The fragment according to claim 1, wherein said fragment is fused to a peptide tag permitting purification.

3. A pharmaceutical, dermatological or nutritional composition comprising said fragment according to claim 1 and a pharmaceutically-acceptable, dermatologically-acceptable, or nutritionally-acceptable carrier.

4. The pharmaceutical, dermatological or nutritional composition according to claim 3, wherein said fragment is contained in an amount in the range of from 0.05 to 5 wt. %, based on the total weight of the composition.

5. The pharmaceutical, dermatological or nutritional composition according to claim 3, wherein the nutritional composition is selected from the group consisting of chocolate, milk, yoghurt, curd, cheese, fermented milks, milk based fermented products, ice-creams, fermented cereal based products, milk based powders, infant formulae and pet food.

6. The pharmaceutical, dermatological or nutritional composition according to claim 3, wherein the dermatological composition is selected from the group consisting of lotions, shampoos, creams, sun-screens, after-sun creams, anti-aging creams, and ointments.

7. The pharmaceutical, dermatological or nutritional composition according to claim 3, wherein the pharmaceutical composition is selected from the group consisting of tablets, liquid suspensions, dried oral supplement, wet oral supplement, dry tube-feeding and wet tube-feeding.

8. The pharmaceutical, dermatological or nutritional composition according to claim 3, wherein the pharmaceutical composition further comprises an excipient selected from the group consisting diluents, binding agents, disintegrants, lubricants, sweeteners, glidants, flavourings and colouring agents.

9. A method for treatment of cancer, atherosclerosis, bacterial infections, inflammations, thromboses and edema, the method comprising: administering a pharmaceutical composition comprising said fragment according to claim 1 to a subject in need of the treatment.

* * * * *